US012611280B2

(12) United States Patent
Kumar et al.

(10) Patent No.: US 12,611,280 B2
(45) Date of Patent: Apr. 28, 2026

(54) SYSTEM, METHOD, AND COMPUTER PROGRAM PRODUCT FOR CUSTOMIZED MEDICAL KIT ASSEMBLY AND INVENTORY MANAGEMENT

(71) Applicant: Becton, Dickinson and Company, Franklin Lakes, NJ (US)

(72) Inventors: Manish Kumar, Bengaluru (IN); Ajay Suryavanshi, Pune (IN); Shishir Prasad, Ramsey, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 781 days.

(21) Appl. No.: 18/094,912

(22) Filed: Jan. 9, 2023

(65) Prior Publication Data

US 2024/0225767 A1     Jul. 11, 2024

(51) Int. Cl.
    *A61B 50/30*       (2016.01)
    *A61B 90/90*       (2016.01)

(52) U.S. Cl.
    CPC .............. *A61B 50/30* (2016.02); *A61B 90/90* (2016.02); *A61J 2205/10* (2013.01)

(58) Field of Classification Search
    CPC ...... A61B 50/30; A61B 90/90; A61J 2205/10; A61L 2103/15; A61L 2202/14; A61L 2/08; A61L 2/081; A61L 2/20; A61L 2/24; G06Q 10/087; G06Q 30/0631; G07F 9/023; G07F 11/00; G07F 11/04; G07F 17/0092; G16H 40/40; G16H 40/20
    See application file for complete search history.

(56) References Cited

U.S. PATENT DOCUMENTS

| | | | | |
|---|---|---|---|---|
| 9,514,131 | B1 * | 12/2016 | Bochenko | .............. G16H 10/40 |
| 2001/0002448 | A1 | 5/2001 | Wilson et al. | |
| 2004/0098286 | A1 | 5/2004 | Zimmerman et al. | |
| 2006/0116355 | A1 * | 6/2006 | Van Breen | ........... A61K 31/685 514/400 |
| 2007/0185615 | A1 * | 8/2007 | Bossi | .................... A61J 7/0084 700/244 |
| 2007/0215515 | A1 * | 9/2007 | Branham | ................. A61F 17/00 206/581 |
| 2008/0166106 | A1 * | 7/2008 | Ozawa | ............... H04N 21/8113 386/245 |
| 2010/0100234 | A1 * | 4/2010 | Osborne | ................. B65B 3/003 700/240 |
| 2010/0152885 | A1 * | 6/2010 | Regan | .................... G01N 35/04 700/228 |
| 2010/0168910 | A1 * | 7/2010 | Haas | ........................ G07F 11/58 700/232 |
| 2012/0273087 | A1 * | 11/2012 | Stavsky | ................ A61J 1/2096 141/2 |

(Continued)

*Primary Examiner* — Michael Collins
(74) *Attorney, Agent, or Firm* — Servilla Whitney LLC

(57) ABSTRACT

Systems, methods, and computer program products for customized medical kit assembly and inventory management are disclosed. A method may include receiving, from a user device, an input associated with a selection of a set of medical devices for a medical kit. The set of medical devices may be dispensed from a storage location in response to receiving the input. The set of medical devices dispensed from the storage location may be packaged at a packaging location to form the medical kit. The medical kit may be dispensed from a fulfillment location.

27 Claims, 7 Drawing Sheets

(56)         References Cited

U.S. PATENT DOCUMENTS

| | | | |
|---|---|---|---|
| 2013/0123974 A1* | 5/2013 | Clarke | G07F 11/62 |
| | | | 700/232 |
| 2014/0156064 A1* | 6/2014 | Crawford | G16H 20/10 |
| | | | 700/236 |
| 2015/0335855 A1* | 11/2015 | Tomes | A61B 50/30 |
| | | | 206/571 |
| 2016/0055307 A1 | 2/2016 | Macoviak et al. | |
| 2019/0083199 A1* | 3/2019 | Cassinis | A61B 50/36 |
| 2019/0163876 A1 | 5/2019 | Remme et al. | |
| 2021/0366604 A1* | 11/2021 | Templeton | G16H 80/00 |
| 2022/0180689 A1* | 6/2022 | Kwon | G07F 11/02 |
| 2024/0304053 A1* | 9/2024 | Dorris | G06Q 20/4014 |

* cited by examiner

200

202

Storage Component
208

Memory
206

Processor
204

Communication
Interface
214

Output Component
212

Input Component
210

300

302  Receive input with selection of a set of medical devices

304  Dispense medical device(s)

306  Package dispensed medical device(s) to form medical kit

308  Dispense medical kit

700

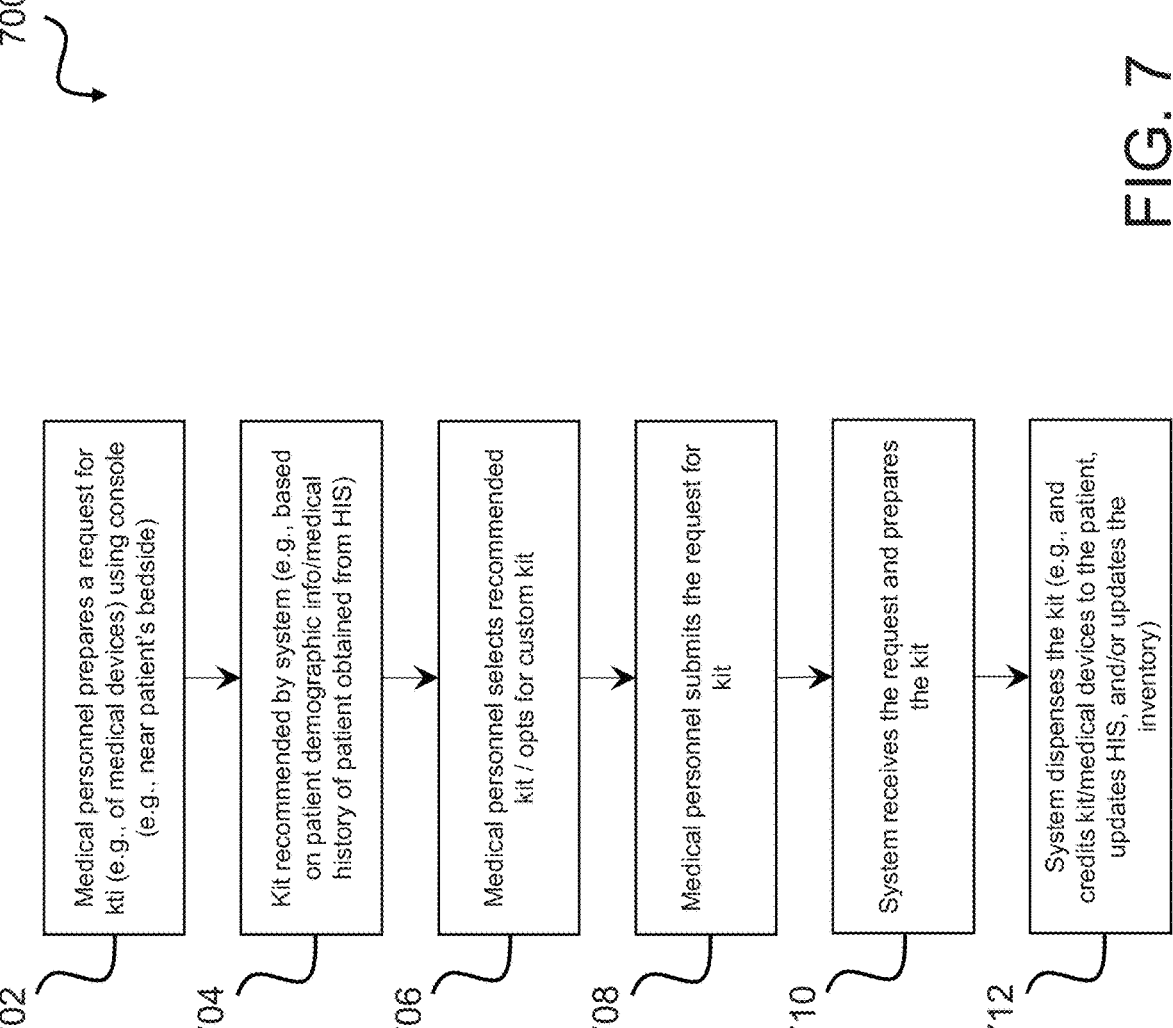

Medical personnel prepares a request for kti (e.g., of medical devices) using console (e.g., near patient's bedside)

702

Kit recommended by system (e.g., based on patient demographic info/medical history of patient obtained from HIS)

704

Medical personnel selects recommended kit / opts for custom kit

706

Medical personnel submits the request for kit

708

System receives the request and prepares the kit

710

System dispenses the kit (e.g. and credits kit/medical devices to the patient, updates HIS, and/or updates the inventory)

SYSTEM, METHOD, AND COMPUTER PROGRAM PRODUCT FOR CUSTOMIZED MEDICAL KIT ASSEMBLY AND INVENTORY MANAGEMENT

BACKGROUND

1. Field

This disclosed subject matter relates generally to medical kit customization and inventory management and, in some embodiments or aspects, to a system, method, and computer program product for customized medical kit assembly and inventory management.

2. Technical Considerations

Certain medical personnel (e.g., clinicians, nurses, support personnel, and/or the like) gather (e.g., pull and/or prep) medical supplies for certain medical procedures. For example, a nurse may gather medical supplies in one room (e.g., a supply room) and then manually carry the medical supplies to another room (e.g., a patient room, an operating room, and/or the like).

However, manually gathering medical supplies and/or manually transporting the medical supplies between rooms may be cumbersome and/or prone to errors. For example, when gathering medical supplies (especially a large number of supplies) before a medical procedure, medical personnel may inadvertently omit an item and/or inadvertently gather too many of one type of item. Even if all of the medical supplies are gathered correctly, the medical personnel may not have access to a suitable container and/or it may be cumbersome to manually load the medical supplies into a container (e.g., trying to fit many oddly shaped items into a bag). Moreover, while transporting the medical supplies, one or more items may be damaged or lost (e.g., especially when a suitable container is unavailable). Additionally, after the medical supplies are gathered and used, medical personnel must manually count the remaining medical supply items in the inventory and/or manually count the items used to subtract them from an inventory.

Premade kits with multiple different medical devices may not be suitable for every clinician and/or every clinical procedure and/or every healthcare setting. For example, different clinicians and/or different hospitals, wards, or medical offices may use different medical supplies for certain medical procedures, so a premade kit suitable for one clinician and/or healthcare setting may not be suitable for another. Stocking many different types of premade kits for different clinicians and/or different healthcare settings may create confusion and/or may result in wasted inventory. In addition, such premade kits must be ordered ahead of time and, therefore, may not be immediately available for use in a medical procedure (e.g., an emergency medical procedure).

SUMMARY

Accordingly, it is an object of the presently disclosed subject matter to provide systems, methods, and computer program products for customized medical kit assembly and inventory management that overcome some or all of the deficiencies identified above.

According to non-limiting embodiments or aspects, provided is a method for customized medical kit assembly and inventory management. For example, a method may include receiving, from a user device, an input associated with a selection of a set of medical devices for a medical kit. The method may include dispensing, from a storage location, the set of medical devices in response to receiving the input. The method may include packaging, at a packaging location, the set of medical devices dispensed from the storage location to form the medical kit. The method may include dispensing, from a fulfillment location, the medical kit.

In some non-limiting embodiments or aspects, the user device may include an input component of a kiosk, wherein the storage location may include a storage grid of the kiosk, wherein the packaging location may include a packaging device of the kiosk, and wherein the fulfillment location may include a fulfillment device of the kiosk.

In some non-limiting embodiments or aspects, the kiosk may include a stationary kiosk.

In some non-limiting embodiments or aspects, the kiosk may include a portable kiosk.

In some non-limiting embodiments or aspects, the portable kiosk may include a robotic kiosk.

In some non-limiting embodiments or aspects, the user device may include an input component of a kiosk, and wherein the input component may include at least one of a touch screen display, a keyboard, a keypad, a mouse, a button, a switch, a microphone, a camera, or any combination thereof.

In some non-limiting embodiments or aspects, the user device may include at least one of a computing device, a portable computing device, a handheld computing device, a personal digital assistant (PDA), a smartphone, a tablet, or any combination thereof.

In some non-limiting embodiments or aspects, the storage location may include a storage grid, the storage grid including a plurality of receptacles, each receptacle containing at least one medical device of a plurality of medical devices, wherein the set of medical devices may include a subset of the plurality of medical devices.

In some non-limiting embodiments or aspects, packaging the set of medical devices may include packaging the set of medical devices in at least one container and/or sealing the at least one container.

In some non-limiting embodiments or aspects, the at least one container may include at least one of a bag, a box, or any combination thereof.

In some non-limiting embodiments or aspects, packaging the set of medical devices may include wrapping the set of medical devices.

In some non-limiting embodiments or aspects, packaging the set of medical devices dispensed from the storage location to form the medical kit may include labeling the medical kit.

In some non-limiting embodiments or aspects, labeling the medical kit may include affixing at least one of a machine-readable optical label, a radio frequency identification (RFID) tag, or any combination thereof to the medical kit.

In some non-limiting embodiments or aspects, the machine-readable optical label may include at least one of a barcode, a quick response (QR) code, or any combination thereof.

In some non-limiting embodiments or aspects, the RFID tag may include at least one of an RFID tag with an integrated circuit (IC) storing identification data, a chipless RFID tag, or any combination thereof.

In some non-limiting embodiments or aspects, the method may further include scanning, at a patient location, the labeled medical kit.

In some non-limiting embodiments or aspects, the method may further include at least one of conveying the set of medical devices dispensed from the storage location to the packaging location and/or conveying the medical kit to the fulfillment location.

In some non-limiting embodiments or aspects, conveying the set of medical devices dispensed from the storage location to the packaging location may include conveying the set of medical devices with at least one of a conveyor belt, a robotic arm, or any combination thereof.

In some non-limiting embodiments or aspects, conveying the medical kit to the fulfillment location may include conveying the medical kit with at least one of a conveyor belt, a robotic arm, or any combination thereof.

In some non-limiting embodiments or aspects, conveying the medical kit to the fulfillment location may include conveying the medical kit with a robotic fulfillment device.

In some non-limiting embodiments or aspects, the method may further include sterilizing, at a sterilization location, the medical kit before dispensing the medical kit.

In some non-limiting embodiments or aspects, sterilizing the medical kit may include sterilizing the medical kit with at least one of electron beam (e-beam) sterilization, ethylene oxide (ETO) sterilization, gamma irradiation sterilization, or any combination thereof.

In some non-limiting embodiments or aspects, the method may further include generating a recommended set of medical devices based on at least one of a selected medical procedure, demographic data associated with a patient, medical history data associated with the patient, preference data associated with a clinician, preference data associated with a facility, medical kit history data associated with the clinician, medical kit history data associated with a facility, or any combination thereof. A graphical user interface including the recommended set of medical devices may be displayed on the user device. Receiving the input associated with the selection of the set of medical devices for the medical kit may include receiving, at the user device, a first input associated with selecting the recommended set of medical devices as the set of medical devices for the medical kit.

In some non-limiting embodiments or aspects, receiving the input associated with the selection of the set of medical devices for the medical kit may include displaying, on the user device, a graphical user interface including a listing of a plurality of medical devices and/or receiving, at the user device, a first input associated with selecting a subset of the plurality of medical devices. The set of medical devices may include the subset of the plurality of medical devices.

In some non-limiting embodiments or aspects, the method may further include crediting the set of medical devices to a patient based on dispensing the medical kit.

In some non-limiting embodiments or aspects, the storage location may store a plurality of medical devices and the set of medical devices may include a subset of the plurality of medical devices, the method further including updating an inventory of medical devices stored at the storage location based on dispensing the medical kit.

According to non-limiting embodiments or aspects, provided is a system for customized medical kit assembly and inventory management. The system may include a user device configured to receive an input associated with a selection of a set of medical devices for a medical kit. The system may include a storage grid configured to dispense the set of medical devices in response to receiving the input. The system may include a packaging device configured to package the set of medical devices dispensed from the storage grid to form the medical kit. The system may include a fulfillment device configured to dispense the medical kit.

In some non-limiting embodiments or aspects, the user device may include an input component of a kiosk, and wherein the kiosk may include the storage grid, the packaging device, and the fulfillment device.

In some non-limiting embodiments or aspects, the kiosk may include a stationary kiosk.

In some non-limiting embodiments or aspects, the kiosk may include a portable kiosk.

In some non-limiting embodiments or aspects, the portable kiosk may include a robotic kiosk.

In some non-limiting embodiments or aspects, the user device may include an input component of a kiosk, and wherein the input component may include at least one of a touch screen display, a keyboard, a keypad, a mouse, a button, a switch, a microphone, a camera, or any combination thereof.

In some non-limiting embodiments or aspects, the user device may include at least one of a computing device, a portable computing device, a handheld computing device, a personal digital assistant (PDA), a smartphone, a tablet, or any combination thereof.

In some non-limiting embodiments or aspects, the storage grid may include a plurality of receptacles, each receptacle containing at least one medical device of a plurality of medical devices, wherein the set of medical devices may include a subset of the plurality of medical devices.

In some non-limiting embodiments or aspects, packaging the set of medical devices may include packaging the set of medical devices in at least one container and/or sealing the at least one container.

In some non-limiting embodiments or aspects, the at least one container may include at least one of a bag, a box, or any combination thereof.

In some non-limiting embodiments or aspects, packaging the set of medical devices may include wrapping the set of medical devices.

In some non-limiting embodiments or aspects, packaging the set of medical devices dispensed from the storage location to form the medical kit may include labeling the medical kit.

In some non-limiting embodiments or aspects, labeling the medical kit may include affixing at least one of a machine-readable optical label, a radio frequency identification (RFID) tag, or any combination thereof to the medical kit.

In some non-limiting embodiments or aspects, the machine-readable optical label may include at least one of a barcode, a quick response (QR) code, or any combination thereof.

In some non-limiting embodiments or aspects, the RFID tag may include at least one of an RFID tag with an integrated circuit (IC) storing identification data, a chipless RFID tag, or any combination thereof.

In some non-limiting embodiments or aspects, the system may further include a scanner configured to scan the labeled medical kit at a patient location.

In some non-limiting embodiments or aspects, the system may further include at least one conveyance device configured to at least one of convey the set of medical devices dispensed from the storage grid to the packaging device and/or convey the medical kit to the fulfillment device.

In some non-limiting embodiments or aspects, the at least one conveyance device may include at least one of a conveyor belt, a robotic arm, or any combination thereof configured to convey the set of medical devices dispensed from the storage grid to the packaging device.

In some non-limiting embodiments or aspects, the at least one conveyance device may include at least one of a conveyor belt, a robotic arm, or any combination thereof configured to convey the medical kit to the fulfillment device.

In some non-limiting embodiments or aspects, the fulfillment device may include a robotic fulfillment device configured to convey the medical kit to a fulfillment location.

In some non-limiting embodiments or aspects, the system may further include at least one sterilization device configured to sterilize the medical kit before the medical kit is dispensed by the fulfillment device.

In some non-limiting embodiments or aspects, the at least one sterilization device may include at least one of an electron beam (e-beam) sterilization device, an ethylene oxide (ETO) sterilization device, a gamma irradiation sterilization device, or any combination thereof.

In some non-limiting embodiments or aspects, the user device may be further configured to generate a recommended set of medical devices based on at least one of a selected medical procedure, demographic data associated with a patient, medical history data associated with the patient, preference data associated with a clinician, preference data associated with a facility, medical kit history data associated with the clinician, medical kit history data associated with the facility, or any combination thereof. The user device may be further configured to display a graphical user interface including the recommended set of medical devices. Receiving the input associated with the selection of the set of medical devices for the medical kit may include receiving a first input associated with selecting the recommended set of medical devices as the set of medical devices for the medical kit.

In some non-limiting embodiments or aspects, the user device may be further configured to display a graphical user interface including a listing of a plurality of medical devices and/or receive a first input associated with selecting a subset of the plurality of medical devices. The set of medical devices may include the subset of the plurality of medical devices.

In some non-limiting embodiments or aspects, the system may further include a health information system configured to credit the set of medical devices to a patient based on dispensing the medical kit.

In some non-limiting embodiments or aspects, the storage grid may be further configured to store a plurality of medical devices and the set of medical devices may include a subset of the plurality of medical devices, the system further may include a health information system configured to update an inventory of medical devices stored by the storage grid based on dispensing the medical kit.

According to non-limiting embodiments or aspects, provided is a computer program product for customized medical kit assembly and inventory management, including at least one non-transitory computer-readable medium including one or more instructions that, when executed by at least one processor, cause the at least one processor to receive, from a user device, an input associated with a selection of a set of medical devices for a medical kit. The one or more instructions, when executed by the at least one processor, may further cause the at least one processor to dispense, from a storage location, the set of medical devices in response to receiving the input. The one or more instructions, when executed by the at least one processor, may further cause the at least one processor to package, at a packaging location, the set of medical devices dispensed from the storage location to form the medical kit. The one or more instructions, when executed by the at least one processor, may further cause the at least one processor to dispense, from a fulfillment location, the medical kit.

Further embodiments or aspects are set forth in the following numbered clauses:

Clause 1: A method for customized medical kit assembly and inventory management, comprising: receiving, from a user device, an input associated with a selection of a set of medical devices for a medical kit; dispensing, from a storage location, the set of medical devices in response to receiving the input; packaging, at a packaging location, the set of medical devices dispensed from the storage location to form the medical kit; and dispensing, from a fulfillment location, the medical kit.

Clause 2: The method of clause 1, wherein the user device comprises an input component of a kiosk, wherein the storage location comprises a storage grid of the kiosk, wherein the packaging location comprises a packaging device of the kiosk, and wherein the fulfillment location comprises a fulfillment device of the kiosk.

Clause 3: The method of clause 1 or clause 2, wherein the kiosk comprises a stationary kiosk.

Clause 4: The method of any of clauses 1-3, wherein the kiosk comprises a portable kiosk.

Clause 5: The method of any of clauses 1-4, wherein the portable kiosk comprises a robotic kiosk.

Clause 6: The method of any of clauses 1-5, wherein the user device comprises an input component of a kiosk, and wherein the input component comprises at least one of a touch screen display, a keyboard, a keypad, a mouse, a button, a switch, a microphone, a camera, or any combination thereof.

Clause 7: The method of any of clauses 1-6, wherein the user device comprises at least one of a computing device, a portable computing device, a handheld computing device, a personal digital assistant (PDA), a smartphone, a tablet, or any combination thereof.

Clause 8: The method of any of clauses 1-7, wherein the storage location comprises a storage grid, the storage grid comprising a plurality of receptacles, each receptacle containing at least one medical device of a plurality of medical devices, wherein the set of medical devices comprises a subset of the plurality of medical devices.

Clause 9: The method of any of clauses 1-8, wherein packaging the set of medical devices comprises: packaging the set of medical devices in at least one container; and sealing the at least one container.

Clause 10: The method of any of clauses 1-9, wherein the at least one container comprises at least one of a bag, a box, or any combination thereof.

Clause 11: The method of any of clauses 1-10, wherein packaging the set of medical devices comprises wrapping the set of medical devices.

Clause 12: The method of any of clauses 1-11, wherein packaging the set of medical devices dispensed from the storage location to form the medical kit comprises labeling the medical kit.

Clause 13: The method of any of clauses 1-12, wherein labeling the medical kit comprises affixing at least one of a machine-readable optical label, a radio frequency identification (RFID) tag, or any combination thereof to the medical kit.

Clause 14: The method of any of clauses 1-13, wherein the machine-readable optical label comprises at least one of a barcode, a quick response (QR) code, or any combination thereof.

Clause 15: The method of any of clauses 1-14, wherein the RFID tag comprises at least one of an RFID tag with an integrated circuit (IC) storing identification data, a chipless RFID tag, or any combination thereof.

Clause 16: The method of any of clauses 1-15, further comprising scanning, at a patient location, the labeled medical kit.

Clause 17: The method of any of clauses 1-16, further comprising at least one of: conveying the set of medical devices dispensed from the storage location to the packaging location; or conveying the medical kit to the fulfillment location.

Clause 18: The method of any of clauses 1-17, wherein conveying the set of medical devices dispensed from the storage location to the packaging location comprises conveying the set of medical devices with at least one of a conveyor belt, a robotic arm, or any combination thereof.

Clause 19: The method of any of clauses 1-18, wherein conveying the medical kit to the fulfillment location comprises conveying the medical kit with at least one of a conveyor belt, a robotic arm, or any combination thereof.

Clause 20: The method of any of clauses 1-19, wherein conveying the medical kit to the fulfillment location comprises conveying the medical kit with a robotic fulfillment device.

Clause 21: The method of any of clauses 1-20, further comprising sterilizing, at a sterilization location, the medical kit before dispensing the medical kit.

Clause 22: The method of any of clauses 1-21, wherein sterilizing the medical kit comprises sterilizing the medical kit with at least one of electron beam (e-beam) sterilization, ethylene oxide (ETO) sterilization, gamma irradiation sterilization, or any combination thereof.

Clause 23: The method of any of clauses 1-22, further comprising: generating a recommended set of medical devices based on at least one of a selected medical procedure, demographic data associated with a patient, medical history data associated with the patient, preference data associated with a clinician, preference data associated with a facility, medical kit history data associated with the clinician, medical kit history data associated with a facility, or any combination thereof; and displaying, at the user device, a graphical user interface comprising the recommended set of medical devices, wherein receiving the input associated with the selection of the set of medical devices for the medical kit comprises receiving, at the user device, a first input associated with selecting the recommended set of medical devices as the set of medical devices for the medical kit.

Clause 24: The method of any of clauses 1-23, wherein receiving the input associated with the selection of the set of medical devices for the medical kit comprises: displaying, on the user device, a graphical user interface comprising a listing of a plurality of medical devices; and receiving, at the user device, a first input associated with selecting a subset of the plurality of medical devices, wherein the set of medical devices comprises the subset of the plurality of medical devices.

Clause 25: The method of any of clauses 1-24, further comprising crediting the set of medical devices to a patient based on dispensing the medical kit.

Clause 26: The method of any of clauses 1-25, wherein the storage location stores a plurality of medical devices and the set of medical devices comprises a subset of the plurality of medical devices, the method further comprising updating an inventory of medical devices stored at the storage location based on dispensing the medical kit.

Clause 27: A system for customized medical kit assembly and inventory management, comprising: a user device configured to receive an input associated with a selection of a set of medical devices for a medical kit; a storage grid configured to dispense the set of medical devices in response to receiving the input; a packaging device configured to package the set of medical devices dispensed from the storage grid to form the medical kit; and a fulfillment device configured to dispense the medical kit.

Clause 28: The system of clause 27, wherein the user device comprises an input component of a kiosk, and wherein the kiosk comprises the storage grid, the packaging device, and the fulfillment device.

Clause 29: The system of clause 27 or clause 28, wherein the kiosk comprises a stationary kiosk.

Clause 30: The system of any of clauses 27-29, wherein the kiosk comprises a portable kiosk.

Clause 31: The system of any of clauses 27-30, wherein the portable kiosk comprises a robotic kiosk.

Clause 32: The system of any of clauses 27-31, wherein the user device comprises an input component of a kiosk, and wherein the input component comprises at least one of a touch screen display, a keyboard, a keypad, a mouse, a button, a switch, a microphone, a camera, or any combination thereof.

Clause 33: The system of any of clauses 27-32, wherein the user device comprises at least one of a computing device, a portable computing device, a handheld computing device, a personal digital assistant (PDA), a smartphone, a tablet, or any combination thereof.

Clause 34: The system of any of clauses 27-33, wherein the storage grid comprises a plurality of receptacles, each receptacle containing at least one medical device of a plurality of medical devices, wherein the set of medical devices comprises a subset of the plurality of medical devices.

Clause 35: The system of any of clauses 27-34, wherein packaging the set of medical devices comprises: packaging the set of medical devices in at least one container; and sealing the at least one container.

Clause 36: The system of any of clauses 27-35, wherein the at least one container comprises at least one of a bag, a box, or any combination thereof.

Clause 37: The system of any of clauses 27-36, wherein packaging the set of medical devices comprises wrapping the set of medical devices.

Clause 38: The system of any of clauses 27-37, wherein packaging the set of medical devices dispensed from the storage location to form the medical kit comprises labeling the medical kit.

Clause 39: The system of any of clauses 27-38, wherein labeling the medical kit comprises affixing at least one of a machine-readable optical label, a radio frequency identification (RFID) tag, or any combination thereof to the medical kit.

Clause 40: The system of any of clauses 27-39, wherein the machine-readable optical label comprises at least one of a barcode, a quick response (QR) code, or any combination thereof.

Clause 41: The system of any of clauses 27-40, wherein the RFID tag comprises at least one of an RFID tag with an integrated circuit (IC) storing identification data, a chipless RFID tag, or any combination thereof.

Clause 42: The system of any of clauses 27-41, further comprising a scanner configured to scan the labeled medical kit at a patient location.

Clause 43: The system of any of clauses 27-42, further comprising at least one conveyance device configured to at least one of: convey the set of medical devices dispensed from the storage grid to the packaging device; or convey the medical kit to the fulfillment device.

Clause 44: The system of any of clauses 27-43, wherein the at least one conveyance device comprises at least one of a conveyor belt, a robotic arm, or any combination thereof configured to convey the set of medical devices dispensed from the storage grid to the packaging device.

Clause 45: The system of any of clauses 27-44, wherein the at least one conveyance device comprises at least one of a conveyor belt, a robotic arm, or any combination thereof configured to convey the medical kit to the fulfillment device.

Clause 46: The system of any of clauses 27-45, wherein the fulfillment device comprises a robotic fulfillment device configured to convey the medical kit to a fulfillment location.

Clause 47: The system of any of clauses 27-46, further comprising at least one sterilization device configured to sterilize the medical kit before the medical kit is dispensed by the fulfillment device.

Clause 48: The system of any of clauses 27-47, wherein the at least one sterilization device comprises at least one of an electron beam (e-beam) sterilization device, an ethylene oxide (ETO) sterilization device, a gamma irradiation sterilization device, or any combination thereof.

Clause 49: The system of any of clauses 27-48, wherein the user device is further configured to: generate a recommended set of medical devices based on at least one of a selected medical procedure, demographic data associated with a patient, medical history data associated with the patient, preference data associated with a clinician, preference data associated with a facility, medical kit history data associated with the clinician, medical kit history data associated with a facility, or any combination thereof; and display a graphical user interface comprising the recommended set of medical devices, wherein receiving the input associated with the selection of the set of medical devices for the medical kit comprises receiving a first input associated with selecting the recommended set of medical devices as the set of medical devices for the medical kit.

Clause 50: The system of any of clauses 27-49, wherein the user device is further configured to: display a graphical user interface comprising a listing of a plurality of medical devices; and receive a first input associated with selecting a subset of the plurality of medical devices, wherein the set of medical devices comprises the subset of the plurality of medical devices.

Clause 51: The system of any of clauses 27-50, further comprising a health information system configured to credit the set of medical devices to a patient based on dispensing the medical kit.

Clause 52: The system of any of clauses 27-51, wherein the storage grid is further configured to store a plurality of medical devices and the set of medical devices comprises a subset of the plurality of medical devices, the system further comprises a health information system configured to update an inventory of medical devices stored by the storage grid based on dispensing the medical kit.

Clause 53: A computer program product for customized medical kit assembly and inventory management, comprising at least one non-transitory computer-readable medium including one or more instructions that, when executed by at least one processor, cause the at least one processor to: receive, from a user device, an input associated with a selection of a set of medical devices for a medical kit; dispense, from a storage location, the set of medical devices in response to receiving the input; package, at a packaging location, the set of medical devices dispensed from the storage location to form the medical kit; and dispense, from a fulfillment location, the medical kit.

These and other features and characteristics of the presently disclosed subject matter, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosed subject matter. As used in the specification and the claims, the singular form of "a," "an," and "the" include plural referents unless the context clearly dictates otherwise.

BRIEF DESCRIPTION OF THE DRAWINGS

Additional advantages and details of the disclosed subject matter are explained in greater detail below with reference to the exemplary embodiments or aspects that are illustrated in the accompanying figures, in which:

FIG. 7 is a flowchart of an example implementation of the systems and/or methods for customized medical kit assembly and inventory management described herein, according to non-limiting embodiments or aspects of the presently disclosed subject matter.

DESCRIPTION

Figure 1:
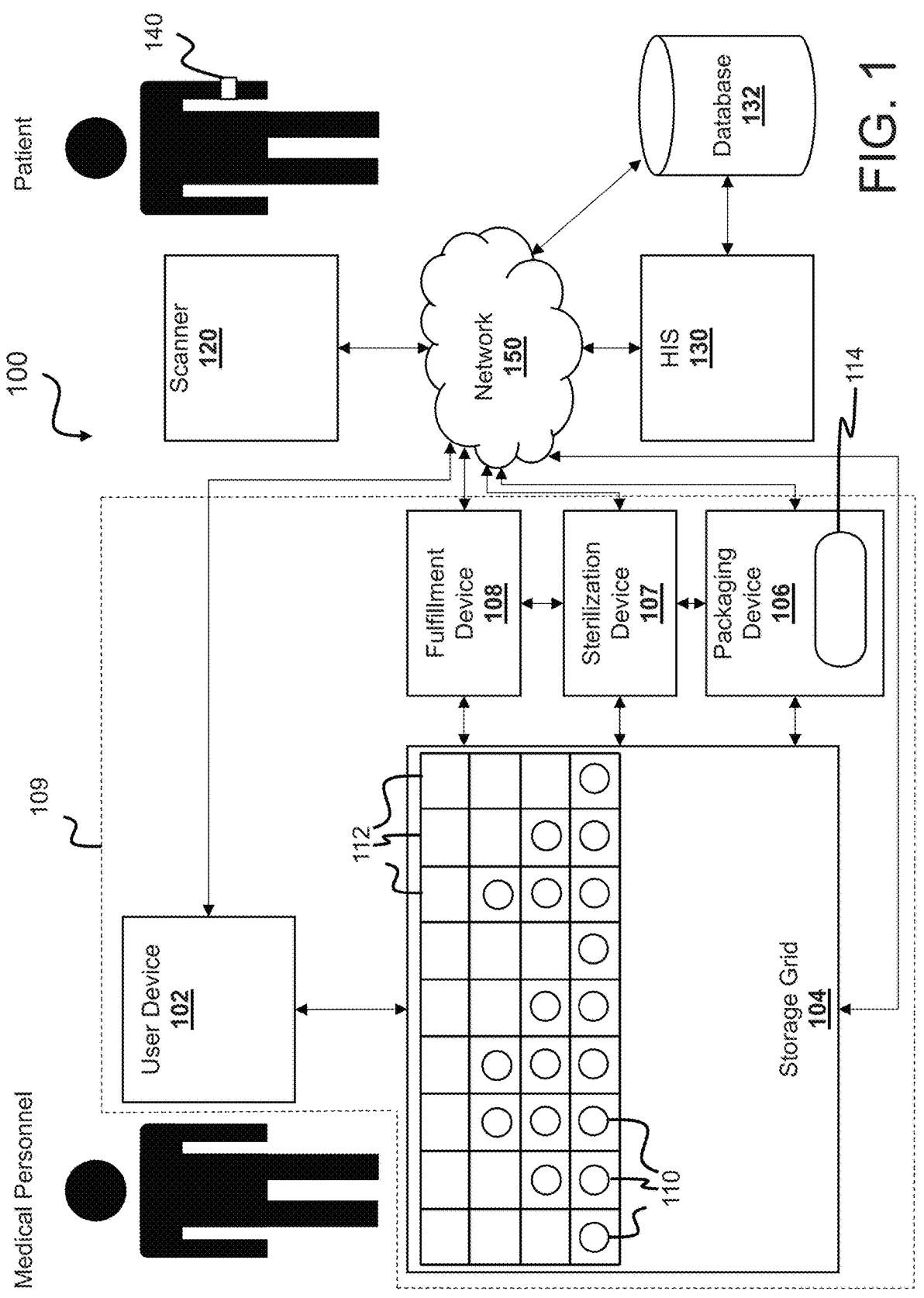
FIG. 1 is a diagram of an example system for customized medical kit assembly and inventory management, according to non-limiting embodiments or aspects of the presently disclosed subject matter.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to the disclosed subject matter as it is oriented in the drawing figures. However, it is to be understood that the disclosed subject matter may assume various alternative variations and step sequences, except where expressly specified to the contrary. It is also to be understood that the specific devices and processes illustrated in the attached drawings, and described in the following specification, are simply exemplary embodiments or aspects of the disclosed subject matter. Hence, specific dimensions and other physical characteristics related to the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Furthermore, as used herein, the term "set" is intended to include one or more items (e.g., related items, unrelated items, a combination of related and unrelated items, and/or the like) and may be used interchangeably with "one or more" or "at least one." Where only one item is intended, the term "one" or similar language is used. Also, as used herein, the terms "has," "have," "having," and/or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments or aspects, a message may refer to a network packet (e.g., a data packet and/or the like) that includes data. It will be appreciated that numerous other arrangements are possible.

As used herein, the term "server" may refer to one or more computing devices, such as processors, storage devices, and/or similar computer components that communicate with client devices and/or other computing devices over a network, such as the Internet or private networks, and, in some examples, facilitate communication among other servers and/or client devices. It will be appreciated that various other arrangements are possible. In addition, reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Non-limiting embodiments or aspects of the disclosed subject matter are directed to systems, methods, and computer program products for medical kit customization and inventory management, including, but not limited to, customized medical kit assembly and inventory management. For example, non-limiting embodiments or aspects of the disclosed subject matter provide receiving an input from a user device associated with a selection of a set of medical devices for a medical kit, dispensing the set of medical devices from a storage location in response to receiving the input, packaging the set of medical devices dispensed from the storage location at a packaging location to form the medical kit, and dispensing the medical kit from a fulfillment location. Such embodiments or aspects enable provision of a customized medical kit of medical devices without requiring manual gathering of the medical devices. As such, the burden on medical personnel in obtaining the medical devices required for a medical procedure is reduced. Additionally, the aforementioned embodiments or aspects reduce the potential for human errors since the medical devices are automatically dispensed (e.g., from a storage grid at the storage location), thereby eliminating inadvertent omissions or inadvertent oversupplying. In addition, the aforementioned embodiments or aspects allow for automatic packaging of the medical devices in the medical kit, thereby ensuring the medical devices are suitably contained (e.g., in a sealed container, a wrap, and/or the like) and can be transported with reduced chance of loss or damage to the medical devices. Moreover, the aforementioned embodiments or aspects allow for the customized medical kit to be available quickly (e.g., in real time, almost immediately, as soon as the medical devices are dispensed and packaged, and/or the like). As such, delays in waiting for shipping (e.g., as compared to premade kits) are reduced (e.g., eliminated). Furthermore, non-limiting embodiments or aspects of the disclosed subject matter provide automatically updating an inventory of medical devices stored at the storage location based on dispensing the medical kit. Such embodiments or aspects reduce (e.g., eliminate) the burden on medical personnel in manually counting and/or tracking inventory. Additionally, non-limiting embodiments or aspects of the disclosed subject matter provide generating a recommended set of medical devices (e.g., for a recommended medical kit) based on at least one of a selected medical procedure, demographic data associated with a patient, medical history data associated with the patient, preference data associated with a clinician, preference data associated with a facility, medical kit history data associated with the clinician, medical kit history data associated with a facility, or any combination thereof. Such embodiments or aspects enable medical personnel (e.g., clinicians) to have the option to quickly select a recommended medical kit and/or to customize a medical kit (e.g., with the recommended set of medical devices as a convenient starting point). In addition, non-limiting embodiments or aspects of the disclosed subject matter provide sterilizing the medical kit at a sterilization location before dispensing the medical kit. Such embodiments or aspects allow for convenient and quick (e.g., in real time, almost immediately, as soon as the medical devices are dispensed and packaged, and/or the like) sterilization of the entire medical kit. Moreover, non-limiting embodiments or aspects of the disclosed subject matter provide labeling the medical kit (e.g., affixing at least one of a machine-readable optical label, a radio frequency identification (RFID) tag, or any combination thereof to the medical kit) and/or scanning the labeled medical kit at a patient location. Such embodiments or aspects enable identification of, tracking of, and/or inventory management based on the medical kit. For example, by scanning the label before opening the medical kit, the medical personnel may ensure that the correct medical kit is being used for the correct patient.

For the purpose of illustration, in the following description, while the presently disclosed subject matter is described with respect to systems, methods, and products for customized medical kit assembly and inventory management, e.g., in a clinical setting, one skilled in the art will recognize that the disclosed subject matter is not limited to the illustrative embodiments or aspects. For example, the systems, methods, and products described herein may be used with a wide variety of settings, such as customized medical kit assembly and/or inventory management in any setting suitable for using such medical kits, e.g., homecare, traveling care, medical offices, medical supply retail locations, any combination thereof, and/or the like.

Referring now to FIG. 1, FIG. 1 is a diagram of an example system 100 for customized medical kit assembly and inventory management, according to non-limiting embodiments or aspects of the presently disclosed subject matter. As shown in FIG. 1, system 100 may include at least one of user device 102, storage grid 104, packaging device 106, sterilization device 107, fulfillment device 108, kiosk 109, medical devices 110, receptacles 112, medical kit 114, scanner 120, health information system 130, database 132, patient identification device 140, network 150, any combination thereof, and/or the like.

User device 102 may include one or more devices capable of receiving information from and/or communicating information to storage grid 104, packaging device 106, sterilization device 107, fulfillment device 108, kiosk 109, scanner 120, health information system 130, database 132, and/or patient identification device 140 (e.g., directly, indirectly via network 150, and/or the like). For example, user device 102 may include at least one computing device, such as a portable and/or handheld device (e.g., a computer, a laptop, a personal digital assistant (PDA), a smartphone, a tablet, and/or the like), a desktop computer, a server, and/or other like devices. In some non-limiting embodiments or aspects, user device 102 may include at least one input component (e.g., a component that permits user device 102 to receive information (e.g., via user input), such as a touch screen display, a keyboard, a keypad, a mouse, a button, a switch, a microphone, a camera, and/or the like). Additionally or alternatively, user device 102 may include at least one output component (e.g., a component that provides output information from user device 102, such as a display, a speaker, one or more light-emitting diodes (LEDs), an antenna, a communication interface, and/or the like). In some non-limiting embodiments or aspects, user device 102 may be connected to, integrated with, part of, and/or part of the same system as at least one of storage grid 104, packaging device 106, sterilization device 107, and/or fulfillment device 108. For example, user device 102 may include an input component of kiosk 109. Additionally or alternatively, kiosk 109 may include at least one of (e.g., all of) storage grid 104, packaging device 106, sterilization device 107, fulfillment device 108, or any combination thereof. In some non-limiting embodiments or aspects, user device 102 may be separate from at least one of (e.g., all of) storage grid 104, packaging device 106, sterilization device 107, fulfillment device 108, and/or kiosk 109.

Storage grid 104 may include one or more devices capable of receiving information from and/or communicating information to user device 102, packaging device 106, sterilization device 107, fulfillment device 108, kiosk 109, scanner 120, health information system 130, database 132, and/or patient identification device 140 (e.g., directly, indirectly via network 150, and/or the like). For example, storage grid 104 may include at least one computing device, such as a server, a group of servers, a desktop computer, and/or other like devices. In some non-limiting embodiments or aspects, storage grid 104 may be connected to, integrated with, and/or part of the same system as at least one of user device 102, packaging device 106, sterilization device 107, and/or fulfillment device 108. For example, kiosk 109 may include storage grid 104. Additionally or alternatively, kiosk 109 may include at least one of (e.g., all of) user device 102, packaging device 106, sterilization device 107, fulfillment device 108, or any combination thereof. In some non-limiting embodiments or aspects, storage grid 104 may be separate from at least one of (e.g., all of) user device 102, packaging device 106, sterilization device 107, fulfillment device 108, and/or kiosk 109.

Packaging device 106 may include one or more devices capable of receiving information from and/or communicating information to user device 102, storage grid 104, sterilization device 107, fulfillment device 108, kiosk 109, scanner 120, health information system 130, database 132, and/or patient identification device 140 (e.g., directly, indirectly via network 150, and/or the like). For example, packaging device 106 may include at least one computing device. In some non-limiting embodiments or aspects, packaging device 106 may be connected to, integrated with, and/or part of the same system as at least one of user device 102, storage grid 104, sterilization device 107, and/or fulfillment device 108. For example, kiosk 109 may include packaging device 106. Additionally or alternatively, kiosk 109 may include at least one of (e.g., all of) user device 102, storage grid 104, sterilization device 107, fulfillment device 108, or any combination thereof. In some non-limiting embodiments or aspects, packaging device 106 may be separate from at least one of (e.g., all of) user device 102, storage grid 104, sterilization device 107, fulfillment device 108, and/or kiosk 109.

Sterilization device 107 may include one or more devices capable of receiving information from and/or communicating information to user device 102, storage grid 104, packaging device 106, fulfillment device 108, kiosk 109, scanner 120, health information system 130, database 132, and/or patient identification device 140 (e.g., directly, indirectly via network 150, and/or the like). For example, sterilization device 107 may include at least one computing device. In some non-limiting embodiments or aspects, sterilization device 107 may be connected to, integrated with, and/or part of the same system as at least one of user device 102, storage grid 104, packaging device 106, and/or fulfillment device 108. For example, kiosk 109 may include sterilization device 107. Additionally or alternatively, kiosk 109 may include at least one of (e.g., all of) user device 102, storage grid 104, packaging device 106, fulfillment device 108, or any combination thereof. In some non-limiting embodiments or aspects, sterilization device 107 may be separate from at least one of (e.g., all of) user device 102, storage grid 104, packaging device 106, fulfillment device 108, and/or kiosk 109.

Fulfillment device 108 may include one or more devices capable of receiving information from and/or communicating information to user device 102, storage grid 104, packaging device 106, sterilization device 107, kiosk 109, scanner 120, health information system 130, database 132, and/or patient identification device 140 (e.g., directly, indirectly via network 150, and/or the like). For example, fulfillment device 108 may include at least one computing device. In some non-limiting embodiments or aspects, fulfillment device 108 may be connected to, integrated with, and/or part of the same system as at least one of user device 102, storage grid 104, packaging device 106, and/or sterilization device 107. For example, kiosk 109 may include fulfillment device 108. Additionally or alternatively, kiosk 109 may include at least one of (e.g., all of) user device 102, storage grid 104, packaging device 106, sterilization device 107, or any combination thereof. In some non-limiting embodiments or aspects, fulfillment device 108 may be separate from at least one of (e.g., all of) user device 102, storage grid 104, packaging device 106, sterilization device 107, and/or kiosk 109.

Kiosk 109 may include one or more devices capable of receiving information from and/or communicating information to user device 102, storage grid 104, packaging device 106, sterilization device 107, fulfillment device 108, scanner 120, health information system 130, database 132, and/or patient identification device 140 (e.g., directly, indirectly via network 150, and/or the like). For example, kiosk 109 may include at least one computing device, such as a server, a group of servers, a desktop computer, and/or other like devices. In some non-limiting embodiments or aspects, kiosk 109 may include at least one of (e.g., all of) user device 102, storage grid 104, packaging device 106, sterilization device 107, and/or fulfillment device 108. In some non-limiting embodiments or aspects, kiosk 109 may be separate from at least one of user device 102, storage grid 104, packaging device 106, sterilization device 107, and/or fulfillment device 108.

Scanner 120 may include one or more devices capable of receiving information from and/or communicating information to user device 102, storage grid 104, packaging device 106, sterilization device 107, fulfillment device 108, kiosk 109, health information system 130, database 132, and/or patient identification device 140 (e.g., directly, indirectly via network 150, and/or the like). For example, scanner 120 may include at least one computing device, such as a portable and/or handheld device (e.g., a computer, a laptop, a PDA, a smartphone, a tablet, and/or the like) and/or other like devices. In some non-limiting embodiments or aspects, scanner 120 may be connected to, integrated with, and/or part of the same system as at least one of user device 102. For example, a portable and/or handheld computing device may include user device 102 and scanner 120. In some non-limiting embodiments or aspects, scanner 120 may be separate from user device 102. In some non-limiting embodiments or aspects, scanner 120 may be capable of receiving information (e.g., from another scanner 120, health information system 130, patient identification device 140, a medical kit 114 (e.g., a label thereof) and/or the like) via a short-range wireless communication connection (e.g., a near-field communication (NFC) communication connection, a radio frequency identification (RFID) communication connection, a Bluetooth® communication connection, a ZigBee® communication connection, and/or the like), and/or communicating information (e.g., to another scanner 120, health information system 130, and/or the like). In some non-limiting embodiments or aspects, scanner 120 may include an optical scanner capable of receiving (e.g., reading) information (e.g., from patient identification device 140, a medical kit 114 (e.g., a label thereof) and/or the like) optically (e.g., via a machine-readable optical label, such as a barcode, a quick response (QR) code, combination thereof, any combination thereof, and/or the like).

Health information system 130 may include one or more devices capable of receiving information from and/or communicating information to user device 102, storage grid 104, packaging device 106, sterilization device 107, fulfillment device 108, kiosk 109, scanner 120, database 132, and/or patient identification device 140 (e.g., directly, indirectly via network 150, and/or the like). For example, health information system 130 may include at least one computing device, such as a server, a group of servers, a desktop computer, a portable and/or handheld device (e.g., a computer, a laptop, a PDA, a smartphone, a tablet, and/or the like), a desktop computer, and/or other like devices. In some non-limiting embodiments or aspects, health information system 130 may be associated with at least one facility (e.g., at least one building, at least one ward, at least one hospital, and/or the like). In some non-limiting embodiments or aspects, health information system 130 may be in communication with at least one data storage device (e.g., database 132 and/or the like), which may be local or remote to health information system 130. In some non-limiting embodiments or aspects, health information system 130 may be capable of receiving information from, storing information in, communicating information to, or searching information stored in the data storage device(s) (e.g., database(s) 132 and/or the like). In some non-limiting embodiments or aspects, health information system 130 may be connected to, integrated with, and/or part of the same system as at least one of user device 102, storage grid 104, packaging device 106, sterilization device 107, and/or fulfillment device 108. For example, health information system 130 may include kiosk 109, which may include at least one of (e.g., all of) user device 102, storage grid 104, packaging device 106, sterilization device 107, fulfillment device 108, or any combination thereof. In some non-limiting embodiments or aspects, health information system 130 may be separate from at least one of (e.g., all of) user device 102, storage grid 104, packaging device 106, sterilization device 107, fulfillment device 108, and/or kiosk 109.

Database 132 may include one or more devices capable of receiving information from and/or communicating information to user device 102, storage grid 104, packaging device 106, sterilization device 107, fulfillment device 108, kiosk 109, scanner 120, health information system 130, and/or patient identification device 140 (e.g., directly, indirectly via network 150, and/or the like). Additionally or alternatively, database 132 may include a data storage device, which may be local or remote to health information system 130. In some non-limiting embodiments or aspects, database 132 may be integrated with (e.g., completely, partially, and/or the like) and/or directly connected to health information system 130. Additionally or alternatively, database 132 may be implemented (e.g., completely, partially, and/or the like) separate from health information system 130. For example, database 132 may be a separate device and/or system from health information system 130. In some non-limiting embodiments or aspects, database 132 and health information system 130 may be associated with the same facility, as described herein. In some non-limiting embodiments or aspects, database 132 may include a computing device, such as a server, a group of servers, a desktop computer, and/or other like devices. In some non-limiting embodiments or aspects, database 132 may include at least one structured query language (SQL) database, at least one non-SQL database, any combination thereof, and/or the like. In some non-limiting embodiments or aspects, database 132 may be capable of retrieving information from, storing information in, communicating information to, or searching information stored in the data storage device.

Each medical device 110 may include at least one device and/or a component thereof configured to be used for medical purposes. For example, each medical device 110 may include at least one device (e.g., instrument, apparatus, implement, machine, contrivance, implant, consumable, any combination thereof, and/or the like) and/or a component thereof, which may be configured for use in the diagnosis of disease or other conditions and/or in the cure, mitigation, treatment, and/or prevention of disease and/or other conditions (e.g., in a human, other animals, and/or the like). In some non-limiting embodiments or aspects, examples of a medical device 110 may include a vascular access device (e.g., intravenous (IV) line, catheter, needle, cannula, and/or the like), a syringe, a catheter (e.g., an angiocath, a urinary catheter, an ablation catheter, an angioplasty catheter, and/or the like), a cutting device (e.g., a scalpel, a drill, a drill bit, a saw, a shaver, a punch, and/or the like), a tourniquet, a clamp, a suction pump, a wound dressing (e.g., gauze, adhesive bandages, non-adhesive bandages, foam transparent film, hydrocolloid, hydrogel, and/or the like), suture thread, a suture needle, surgical staples, surgical drapes, other consumable medical supplies, any combination thereof, and/or the like.

Patient identification device 140 may include one or more devices capable of receiving information from and/or communicating information to user device 102, storage grid 104, packaging device 106, sterilization device 107, fulfillment device 108, kiosk 109, scanner 120, health information system 130, and/or database 132 (e.g., directly, indirectly via network 150, and/or the like). For example, patient identification device 140 may include at least one machine-readable optical label (e.g., barcode, QR code, and/or the like), at least one RFID tag (e.g., an RFID tag with an integrated circuit (IC) storing identification data thereof, a chipless RFID tag, any combination thereof, and/or the like), a computing device (e.g., a portable and/or handheld device, such as a smartphone, a tablet, and/or the like), any combination thereof, and/or the like. In some non-limiting embodiments or aspects, patient identification device 140 may be wearable by a patient. For example, patient identification device 140 may include a badge, a bracelet, a watch, glasses, one or more lenses, clothing, and/or the like.

Network 150 may include at least one communication network. For example, network 150 may include a wired network, a wireless network, a cellular network (e.g., a long-term evolution (LTE) network, a third generation (3G) network, a fourth generation (4G) network, a fifth generation (5G) network, a code division multiple access (CDMA) network, and/or the like), a public land mobile network (PLMN), a local area network (LAN), a wide area network (WAN), a metropolitan area network (MAN), a telephone network (e.g., the public switched telephone network (PSTN)), a private network (e.g., a private network associated with a facility), an ad hoc network, an intranet, the Internet, a fiber optic-based network, a computer network, a cloud computing network, and/or the like, and/or a combination of these or other types of networks.

In some non-limiting embodiments or aspects, user device 102 may be configured to receive an input associated with a selection of a set of medical devices 110 for a medical kit 114. Storage grid 104 may be configured to dispense the set of medical devices 110 in response to receiving the input (e.g., in response to user device 102 receiving the input and/or in response to user device 102 communicating medical device selection data associated with the input to storage grid 104 and storage grid 104 receiving the medical device selection data). Packaging device 106 may be configured to package the set of medical devices 110 dispensed from storage grid 104 to form medical kit 114. Fulfillment device 108 may be configured to dispense medical kit 114.

In some non-limiting embodiments or aspects, user device 102 may include an input component of kiosk 109. Additionally or alternatively, kiosk 109 may include storage grid 104, packaging device 106, and/or fulfillment device 108.

In some non-limiting embodiments or aspects, kiosk 109 may include a stationary kiosk. For example, kiosk 109 may be stationary at a location within a facility, as described herein.

In some non-limiting embodiments or aspects, kiosk 109 may include a portable kiosk. For example, kiosk 109 may be configured to move and/or be moved to different locations within a facility, as described herein. In some non-limiting embodiments or aspects, the portable kiosk may include a robotic kiosk, as described herein.

In some non-limiting embodiments or aspects, user device 102 may include an input component of kiosk 109. For example, the input component may include at least one of a touch screen display, a keyboard, a keypad, a mouse, a button, a switch, a microphone, a camera, or any combination thereof, as described herein.

In some non-limiting embodiments or aspects, user device 102 may include at least one of a computing device, a portable computing device, a handheld computing device, a personal digital assistant (PDA), a smartphone, a tablet, or any combination thereof, as described herein. For example, such a user device 102 may be separate from at least one of (e.g., all of) storage grid 104, packaging device 106, sterilization device 107, fulfillment device 108, and/or kiosk 109.

In some non-limiting embodiments or aspects, user device 102 and/or health information system 130 may be configured to generate a recommended set of medical devices 110. For example, user device 102 and/or health information system 130 may generate the recommended set of medical devices 110 based on input received from a user (e.g., medical personnel, such as a nurse, a clinician, and/or the like) and/or data stored in database 132. For example, the input received from the user and/or data stored in database 132 may include at least one of a selected medical procedure, demographic data associated with a patient, medical history data associated with the patient, preference data associated with a clinician, preference data associated with a facility, medical kit history data associated with the clinician, medical kit history data associated with the facility, any combination thereof, and/or the like. In some non-limiting embodiments or aspects, user device 102 may display a graphical user interface including the recommended set of medical devices 110. For example, receiving the input associated with the selection of the selected set of medical devices 110 for medical kit 114 may include receiving a first input (e.g., via the graphical user interface) associated with selecting the recommended set of medical devices 110 as the selected set of medical devices for medical kit 114 (e.g., the user selects the medical devices 110 as recommended by user device 102 and/or health information system 130). Alternatively, user device 102 may receive a second input (e.g., via the graphical user interface) indicating that the user is not selecting the recommended set of medical devices 110 and/or indicating that the user would like to select a custom set of medical devices 110 for medical kit 114.

In some non-limiting embodiments or aspects, user device 102 may display a graphical user interface including a listing of a plurality of medical devices stored by storage grid 104 (e.g., in receptacles 112 thereof). For example, receiving the input associated with the selection of the selected set of medical devices 110 for medical kit 114 may include an input associated with selecting a subset of the plurality of medical devices 110 (e.g., the user selects one or more medical devices 110 from the listing displayed in the graphical user interface). For example, the selected set of medical devices 110 for medical kit 114 may include the subset of the plurality of medical devices 110 selected via the graphical user interface displayed on user device 102.

In some non-limiting embodiments or aspects, storage grid 104 may include a plurality of receptacles 112. For example, each receptacle 112 may contain at least one medical device 110 of a plurality of medical devices 110. In some non-limiting embodiments or aspects, the set of medical devices 110 selected for inclusion in medical kit 114 may be a subset of the plurality of medical devices 110 stored by storage grid 104.

In some non-limiting embodiments or aspects, packaging device 106 may package the selected set of medical devices 110 in at least one container. Additionally or alternatively, packaging device 106 may seal the container(s). For example, medical kit 114 may include the sealed container(s) with the selected set of medical devices 110 therein. In some non-limiting embodiments or aspects, the container(s) may include at least one of a bag, a box, or any combination thereof.

In some non-limiting embodiments or aspects, packaging device 106 may package the selected set of medical devices 110 by wrapping the selected set of medical devices 110. For example, packaging device 106 may wrap the selected set of medical devices 110 in plastic, fabric, tape, or any other suitable material.

In some non-limiting embodiments or aspects, packaging device 106 may label medical kit 114 (e.g., as part of and/or after the packaging of the selected set of medical devices 110). For example, labeling the medical kit 114 may include affixing at least one of a machine-readable optical label, a radio frequency identification (RFID) tag, or any combination thereof to the medical kit 114. For example, affixing may include printing a label on medical kit 114, adhering an adhesive label (e.g., machine-readable optical label) and/or tag (e.g., RFID tag) to medical kit 114, and/or the like. In some non-limiting embodiments or aspects, the machine-readable optical label may include at least one of a barcode, a quick response (QR) code, or any combination thereof. In some non-limiting embodiments or aspects, the RFID tag may include at least one of an RFID tag with an integrated circuit (IC) storing identification data, a chipless RFID tag, or any combination thereof.

In some non-limiting embodiments or aspects, at least one conveyance device may be configured to convey the set of medical devices 110 dispensed from storage grid 104 to packaging device 106, as described herein. For example, the conveyance device(s) may include at least one of a conveyor belt, a robotic arm, or any combination thereof configured to convey the set of medical devices 110 dispensed from storage grid 104 to packaging device 106. Additionally or alternatively, at least one conveyance device may be configured to convey medical kit 114 to sterilization device 107 and/or fulfillment device 108, as described herein. For example, the conveyance device(s) may include at least one of a conveyor belt, a robotic arm, or any combination thereof configured to convey medical kit 114 to sterilization device 107 and/or fulfillment device 108.

In some non-limiting embodiments or aspects, fulfillment device 108 may include a robotic fulfillment device configured to convey medical kit 114 to a fulfillment location (e.g., a location of the patient within the facility).

In some non-limiting embodiments or aspects, sterilization device 107 may be configured to sterilize medical kit 114 (e.g., before medical kit 114 is dispensed by fulfillment device 108). For example, sterilization device 107 may include at least one of an electron beam (e-beam) sterilization device, an ethylene oxide (ETO) sterilization device, a gamma irradiation sterilization device, or any combination thereof.

In some non-limiting embodiments or aspects, scanner 120 may be configured to scan the labeled medical kit 114 (e.g., optically scan the machine-readable optical label, electromagnetically scan the RFID tag, and/or the like) at a patient location. For example, medical personnel (e.g., a clinician, nurse, and/or the like) may scan medical kit 114 with scanner 120. Additionally or alternatively, the medical personnel may scan patient identification device 140 with scanner 120. In some non-limiting embodiments or aspects, scanner 120 may communicate scanned label data associated with scanning medical kit 114 and/or patient identification data associated with scanning patient identification device 140 to health information system 130. In some non-limiting embodiments or aspects, scanner 120 and/or health information system 130 may determine that the scanned medical kit 114 is the appropriate medical kit 114 for the patient identified by the patient identification device 140. In some non-limiting embodiments or aspects, in response to determining the scanned medical kit 114 is not appropriate for the patient identified by the patient identification device 140, scanner 120 and/or health information system 130 may communicate an alert (e.g. to scanner 120, to user device 102, and/or the like). For example, scanner 120 and/or user device 102 may display a message and/or produce an output (e.g., an audible output from a speaker, a visual output from a visual indicator such as a light and/or an LED, and/or the like) based on the alert.

In some non-limiting embodiments or aspects, health information system 130 may be configured to credit the set of medical devices 110 (e.g., medical kit 114) to a patient based on dispensing medical kit 114 (e.g., from fulfillment device 108). Additionally or alternatively, health information system 130 may be configured to credit the set of medical devices 110 (e.g., medical kit 114) to the patient based on scanning the labeled medical kit 114 at the patient location, as described herein.

In some non-limiting embodiments or aspects, storage grid 104 and/or health information system 130 may maintain (e.g., store, track, update, and/or the like) an inventory of medical devices 110 stored by storage grid 104. For example, the inventory may include inventory data associated with the plurality of medical devices 110 stored by storage grid 104. In some non-limiting embodiments or aspects, storage grid 104 and/or health information system 130 may be configured to update the inventory of medical devices 110 stored by storage grid 104 based on dispensing medical kit 114.

The number and arrangement of systems, devices, and/or networks shown in FIG. 1 are provided as an example. There may be additional systems, devices, and/or networks; fewer systems, devices, and/or networks; different systems, devices, and/or networks; and/or differently arranged systems, devices, and/or networks than those shown in FIG. 1. Furthermore, two or more systems or devices shown in FIG. 1 may be implemented within a single system or device, or a single system or device shown in FIG. 1 may be implemented as multiple, distributed systems or devices. Additionally or alternatively, a set of systems (e.g., one or more systems) or a set of devices (e.g., one or more devices) of system 100 may perform one or more functions described as being performed by another set of systems or another set of devices of system 100.

Figure 2:
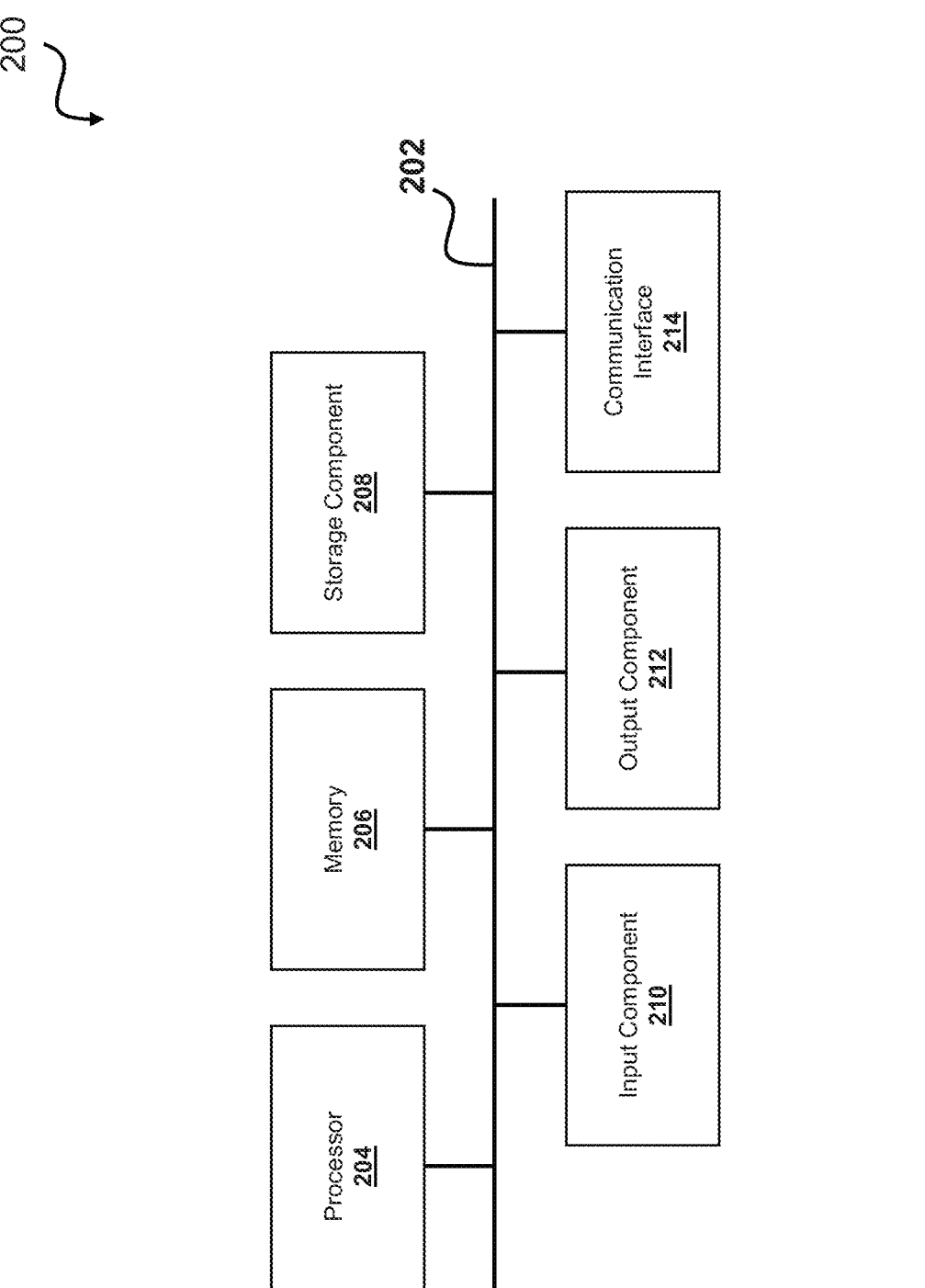
FIG. 2 is a diagram of example components of one or more devices of FIG. 1, according to non-limiting embodiments or aspects of the presently disclosed subject matter.

Referring now to FIG. 2, FIG. 2 is a diagram of example components of a device 200, according to non-limiting embodiments or aspects of the presently disclosed subject matter. Device 200 may correspond to user device 102, storage grid 104, packaging device 106, sterilization device 107, fulfillment device 108, kiosk 109, scanner 120, health information system 130 (e.g., one or more devices of health information system 130), database 132, and/or patient identification device 140. In some non-limiting embodiments or aspects, user device 102, storage grid 104, packaging device 106, sterilization device 107, fulfillment device 108, kiosk 109, scanner 120, health information system 130, database 132, and/or patient identification device 140 may include at least one device 200 and/or at least one component of device 200. As shown in FIG. 2, device 200 may include bus 202, processor 204, memory 206, storage component 208, input component 210, output component 212, and communication interface 214.

Bus 202 may include a component that permits communication among the components of device 200. In some non-limiting embodiments or aspects, processor 204 may be implemented in hardware, software, firmware, and/or any combination thereof. For example, processor 204 may include a processor (e.g., a central processing unit (CPU), a graphics processing unit (GPU), an accelerated processing unit (APU), and/or the like), a microprocessor, a digital signal processor (DSP), and/or any processing component (e.g., a field-programmable gate array (FPGA), an application-specific integrated circuit (ASIC), and/or the like), and/or the like, which can be programmed to perform a function. Memory 206 may include random access memory (RAM), read-only memory (ROM), and/or another type of dynamic or static storage device (e.g., flash memory, magnetic memory, optical memory, and/or the like) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, and/or the like), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, a camera, and/or the like). Additionally or alternatively, input component 210 may include an antenna for receiving electromagnetic radiation, a sensor for sensing information (e.g., a global positioning system (GPS) component, an accelerometer, a gyroscope, an actuator, and/or the like), and/or the like. Output component 212 may include a component that provides output information from device 200 (e.g., an antenna for transmitting electromagnetic radiation, a display, a speaker, one or more light-emitting diodes (LEDs), and/or the like).

Communication interface 214 may include a transceiver-like component (e.g., a transceiver, a receiver and transmitter that are separate, and/or the like) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi® interface, a Bluetooth® interface, a ZigBee® interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

The number and arrangement of components shown in FIG. 2 are provided as an example. In some non-limiting embodiments or aspects, device 200 may include additional components, fewer components, different components, or differently arranged components than those shown in FIG. 2. Additionally or alternatively, a set of components (e.g., one or more components) of device 200 may perform one or more functions described as being performed by another set of components of device 200.

Figure 3:
FIG. 3 is a flowchart of an example process for customized medical kit assembly and inventory management, according to non-limiting embodiments or aspects of the presently disclosed subject matter.
Figure 3:
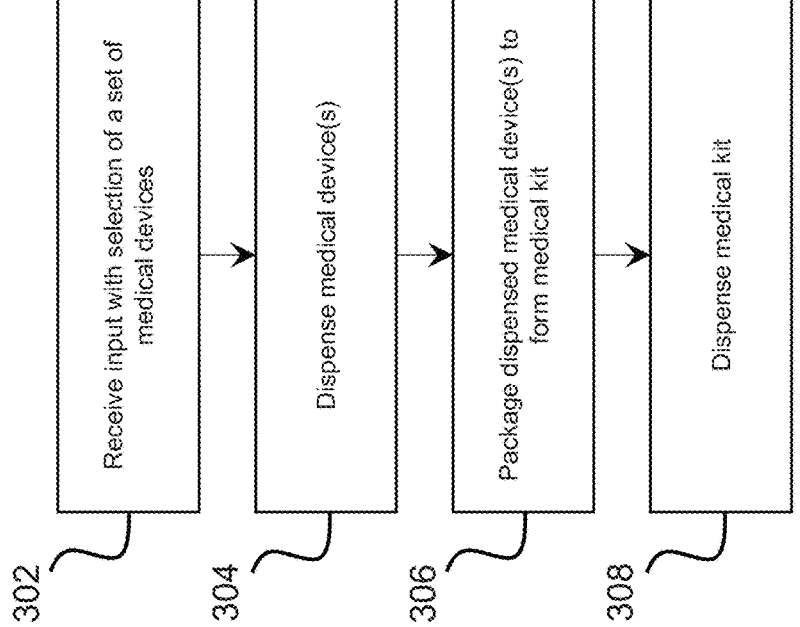
Figure 3:

Referring now to FIG. 3, FIG. 3 is a flowchart of an example process 300 for customized medical kit assembly and inventory management, according to non-limiting embodiments or aspects of the presently disclosed subject matter. In some non-limiting embodiments or aspects, one or more of the steps of process 300 may be performed (e.g., completely, partially, and/or the like) by kiosk 109 (e.g., one or more devices of kiosk 109, such as user device 102, storage grid 104, packaging device 106, sterilization device 107, fulfillment device 108, and/or the like). In some non-limiting embodiments or aspects, one or more of the steps of process 300 may be performed (e.g., completely, partially, and/or the like) by another system, another device, another group of systems, or another group of devices, separate from or including kiosk 109, such as user device 102, storage grid 104, packaging device 106, sterilization device 107, fulfillment device 108, scanner 120, health information system 130 (e.g., one or more devices of health information system 130), database 132, and/or patient identification device 140. The number and arrangement of steps shown in FIG. 3 are provided as an example. In some non-limiting embodiments or aspects, process 300 may include additional steps, fewer steps, different steps, or differently arranged steps than those shown in FIG. 3.

As shown in FIG. 3, at step 302, process 300 may include receiving input with a selection of a set of medical devices. For example, kiosk 109 and/or user device 102 may receive an input associated with a selection of a set of medical devices 110 for a medical kit 114, as described herein. For example, user device 102 may receive the input. Additionally or alternatively, user device 102 may communicate medical device selection data associated with the input to kiosk 109 and/or storage grid 104.

In some non-limiting embodiments or aspects, user device 102 may include an input component of kiosk 109, as described herein. In some non-limiting embodiments or aspects, kiosk 109 may include a stationary kiosk, as described herein. Additionally or alternatively, kiosk 109 may include a portable kiosk, as described herein. For example, the portable kiosk may include a robotic kiosk.

In some non-limiting embodiments or aspects, user device 102 may include at least one computing device, such as a portable and/or handheld computing device, as described herein. For example, such a user device 102 may be separate from at least one of (e.g., all of) storage grid 104, packaging device 106, sterilization device 107, fulfillment device 108, and/or kiosk 109, as described herein.

In some non-limiting embodiments or aspects, kiosk 109, user device 102, and/or health information system 130 may generate a recommended set of medical devices 110, as described herein. For example, kiosk 109, user device 102, and/or health information system 130 may generate the recommended set of medical devices 110 based on input received from a user (e.g., medical personnel, such as a nurse, a clinician, and/or the like) and/or data stored in database 132, as described herein. For example, the input received from the user and/or data stored in database 132 may include at least one of a selected medical procedure, demographic data associated with a patient, medical history data associated with the patient, preference data associated with a clinician, preference data associated with a facility, medical kit history data associated with the clinician, medical kit history data associated with the facility, any combination thereof, and/or the like. In some non-limiting embodiments or aspects, kiosk 109, user device 102, and/or health information system 130 may display a graphical user interface comprising the recommended set of medical devices, as described herein. For example, receiving the input associated with the selection of the selected set of medical devices 110 for medical kit 114 may include receiving a first input (e.g., via the graphical user interface) associated with selecting the recommended set of medical devices 110 as the selected set of medical devices for medical kit 114 (e.g., the user selects the medical devices 110 as recommended by kiosk 109, user device 102 and/or health information system 130). Alternatively, kiosk 109, user device 102 and/or health information system 130 may receive a second input (e.g., via the graphical user interface) indicating that the user is not selecting the recommended set of medical devices 110 and/or indicating that the user would like to select a custom set of medical devices 110 for medical kit 114.

In some non-limiting embodiments or aspects, kiosk 109, user device 102 and/or health information system 130 may display a graphical user interface including a listing of a plurality of medical devices stored by storage grid 104 (e.g., in receptacles 112 thereof), as described herein. For example, the graphical user interface including the listing of medical devices may be displayed in response to receiving the second input (e.g., via the graphical user interface) indicating that the user is not selecting the recommended set of medical devices 110 and/or indicating that the user would like to select a custom set of medical devices 110 for medical kit 114. In some non-limiting embodiments or aspects, receiving the input associated with the selection of the selected set of medical devices 110 for medical kit 114 may include receiving a third input associated with selecting a subset of the plurality of medical devices 110 (e.g., the user selects one or more medical devices 110 from the listing displayed in the graphical user interface). For example, the selected set of medical devices 110 for medical kit 114 may include the subset of the plurality of medical devices 110 selected via the graphical user interface displayed on user device 102.

As shown in FIG. 3, at step 304, process 300 may include dispensing at least one medical device from a storage location. For example, kiosk 109 and/or storage grid 104 may dispense the set of medical devices from a storage location (e.g., storage grid 104 and/or receptacles 112) in response to the input received by user device 102 and/or kiosk 109 (and/or in response to user device 102 communicating medical device selection data associated with the input to kiosk 109 and/or storage grid 104), as described herein.

In some non-limiting embodiments or aspects, the storage location may include storage grid 104, which may include receptacles 112, as described herein. Each receptacle 112 may contain at least one medical device of a plurality of medical devices 110, as described herein. For example, the set of medical devices 110 dispensed from the storage location may include a subset of the plurality of medical devices 110, as described herein.

In some non-limiting embodiments or aspects, the set of medical devices 110 dispensed from the storage location (e.g., storage grid 104 and/or receptacles 112) may be conveyed to a packaging location (e.g., packaging device 106). For example, conveying the set of medical devices 110 dispensed from the storage location to the packaging location may include conveying the set of medical devices 110 with at least one of a conveyor belt, a robotic arm, or any combination thereof, as described herein.

As shown in FIG. 3, at step 306, process 300 may include packaging at least one medical device to form a medical kit. For example, kiosk 109 and/or packaging device 106 may package the set of medical devices 110 dispensed from the storage location at a packaging location (e.g., packaging device 106) to form medical kit 114, as described herein.

In some non-limiting embodiments or aspects, packaging the set of medical devices 110 may include packaging (e.g., by kiosk 109 and/or packaging device 106) the set of medical devices 110 in at least one container and/or sealing the container(s), as described herein. For example, the container may include at least one of a bag, a box, or any combination thereof.

In some non-limiting embodiments or aspects, packaging the set of medical devices 110 may include wrapping (e.g., by kiosk 109 and/or packaging device 106) the set of medical devices 110, as described herein.

In some non-limiting embodiments or aspects, packaging the set of medical devices 110 may include labeling medical kit 114, as described herein. For example, labeling medical kit 114 may include affixing at least one of a machine-readable optical label, an RFID tag, any combination thereof, and/or the like to medical kit 114, as described herein. In some non-limiting embodiments or aspects, the machine-readable optical label may include at least one of a barcode, a QR code, any combination thereof, and/or the like. In some non-limiting embodiments or aspects, the RFID tag may include at least one of an RFID tag with an IC storing identification data, a chipless RFID tag, any combination thereof, and/or the like.

In some non-limiting embodiments or aspects, medical kit 114 may be conveyed to a fulfillment location, as described herein. For example, conveying medical kit 114 to the fulfillment location may include conveying the medical kit 114 with at least one of a conveyor belt, a robotic arm, or any combination thereof. Additionally or alternatively, conveying the medical kit 114 to the fulfillment location may include conveying the medical kit 114 with fulfillment device 108, which may be a robotic fulfillment device, as described herein.

In some non-limiting embodiments or aspects, medical kit 114 may be sterilized at a sterilization location (e.g., before dispensing medical kit 114), as described herein. For example, sterilizing the medical kit 114 may include sterilizing the medical kit 114 with sterilization device 107, which may perform at least one of e-beam sterilization, ETO sterilization, gamma irradiation sterilization, any combination thereof, and/or the like.

As shown in FIG. 3, at step 308, process 300 may include dispensing a medical kit 114. For example, kiosk 109 and/or fulfillment device 108 may dispense medical kit 114 from and/or at a fulfillment location, as described herein.

In some non-limiting embodiments or aspects, medical kit 114 (e.g., which may be labeled, as described herein) may be scanned (e.g., by scanner 120) at a patient location, as described herein.

In some non-limiting embodiments or aspects, kiosk 109 and/or health information system 130 may credit the set of medical devices 110 and/or medical kit 114 to a patient based on dispensing the medical kit 114 (and/or based on scanning medical kit 114 at the patient location), as described herein.

In some non-limiting embodiments or aspects, kiosk 109, storage grid 104, and/or health information system 130 may update an inventory of medical devices stored at the storage location (e.g., storage grid 104) based on dispensing the medical kit 114 (and/or based on scanning medical kit 114 at the patient location), as described herein.

Figure 4:
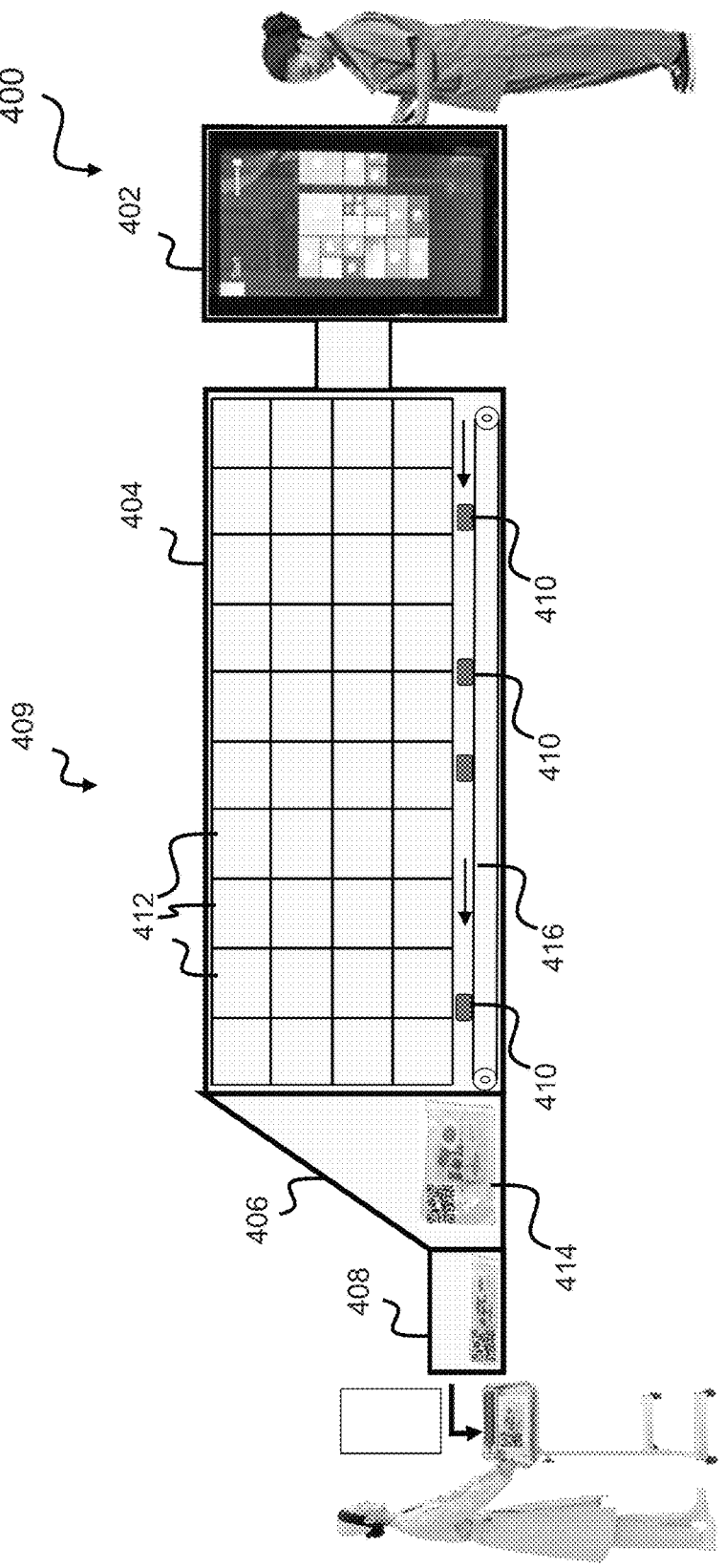
FIG. 4 is a diagram of an example implementation of the systems and/or methods for customized medical kit assembly and inventory management described herein, according to non-limiting embodiments or aspects of the presently disclosed subject matter.

Referring now to FIG. 4, FIG. 4 is a diagram of an example implementation 400 of the systems and/or methods for customized medical kit assembly and inventory management described herein, according to non-limiting embodiments or aspects of the presently disclosed subject matter. As shown in FIG. 4, implementation 400 may include user device 402, storage grid 404, packaging device 406, sterilization and fulfillment device 408, kiosk 409, medical devices 410, receptacles 412, medical kit 414, and/or conveyance device 416. In some non-limiting embodiments or aspects, user device 402 may be the same as or similar to user device 102. In some non-limiting embodiments or aspects, storage grid 404 may be the same as or similar to storage grid 104. In some non-limiting embodiments or aspects, packaging device 406 may be the same as or similar to packaging device 106. In some non-limiting embodiments or aspects, sterilization and fulfillment device 408 may be the same as or similar to sterilization device 107 and/or fulfillment device 108. In some non-limiting embodiments or aspects, kiosk 409 may be the same as or similar to kiosk 109. In some non-limiting embodiments or aspects, medical devices 410 may be the same as or similar to medical devices 110. In some non-limiting embodiments or aspects, receptacles 412 may be the same as or similar to receptacles 112. In some non-limiting embodiments or aspects, medical kit 414 may be the same as or similar to medical kit 114. The number and arrangement of components shown in FIG. 4 are provided as an example. In some non-limiting embodiments or aspects, implementation 400 may include additional components, fewer components, different components, or differently arranged components than those shown in FIG. 4. Additionally or alternatively, a set of components (e.g., one or more components) of implementation 400 may perform one or more functions described as being performed by another set of components of implementation 400.

As shown in FIG. 4, kiosk 409 may include user device 402, storage grid 404, packaging device 406, and sterilization and fulfillment device 408. For example, user device 402, storage grid 404, packaging device 406, and sterilization and fulfillment device 408 each may be part of kiosk 409.

In some non-limiting embodiments or aspects, kiosk 409 may include a smart vending machine for temporary storage (until dispensed) of medical devices 410, automated inventory maintenance, and dispensing of packaged custom medical kits 414 of medical devices 410, for example, on a patient-by-patient and/or procedure-by-procedure basis, e.g., based on input from medical personnel, such as clinician, nurse, and/or other medical support staff.

In some non-limiting embodiments or aspects, kiosk 409 (e.g., user device 402 thereof) may be configured to receive an input associated with a selection of a set of medical devices 410 for medical kit 414, as described herein. Additionally or alternatively, kiosk 409 (e.g., storage grid 404 thereof) may be configured to dispense the set of medical devices 410 in response to receiving the input (e.g., in response to user device 402 receiving the input), as described herein. Additionally or alternatively, kiosk 409 (e.g., packaging device 406 thereof) may be configured to package the set of medical devices 410 (e.g., dispensed from storage grid 404) to form medical kit 414 and/or label medical kit 414, as described herein. Additionally or alternatively, kiosk 409 (e.g., sterilization and fulfillment device 408 thereof) may be configured to sterilize medical kit 414 and/or dispense medical kit 414, as described herein.

In some non-limiting embodiments or aspects, conveyance device 416 may convey the set of medical devices 410 to packaging device 406. For example, conveyance device 416 may include a conveyor belt. Additionally or alternatively, conveyance device 416 may convey medical kit 414 to sterilization and fulfillment device 408.

In some non-limiting embodiments or aspects, kiosk 409 may reduce workflow steps for medical personnel. For example, a nurse may receive a final, packaged, customized medical kit 414 (e.g., dispensed from sterilization and fulfillment device 408) to be carried to a patient location (e.g., bedside, operating room, operating table, clinician office, and/or the like) without the need for manual kitting. Additionally or alternatively, kiosk 409 may enable automated inventory management, as described herein. Additionally or alternatively, kiosk 409 may enable a clinician (e.g., doctor and/or the like) to control selection of medical devices 410 for a customized medical kit 414 for a specific patient and/or a specific procedure, as described herein.

In some non-limiting embodiments or aspects, kiosk 409 may avoid burdens on medical personnel and/or manual errors, e.g., from do-it-yourself (DIY) kitting, as described herein. For example, input from the medical personnel may be automated, e.g., directly inputted into kiosk 409 (e.g., user device 402 thereof), thereby reducing manual errors in input and output (e.g., medical kit 414). Additionally or alternatively, kiosk 409 may allow for traceability based on the label (e.g., barcode, QR code, RFID tag, and/or the like) on each customized medical kit 414, as described herein.

In some non-limiting embodiments or aspects, kiosk 409 may enable medical personnel to select a customized set of medical devices 410 (e.g., medical devices from different suppliers and/or manufacturers, medical consumables, etc.) to be included in the customized medical kit 414, as described herein. Additionally or alternatively, kiosk 409 may enable medical personnel to select a recommended set of medical devices 410 to be included in medical kit 414.

In some non-limiting embodiments or aspects, kiosk 409 and/or user device 402 may recommend medical devices 410 to be included in medical kit 414 based on a smart algorithm. For example, the smart algorithm may recommend medical devices 410 to be included in medical kit 414 based on one or more inputs, such as patient type, patient age, patient gender, co-morbidities, patient medical history, procedure type, historical clinical practice at a facility (e.g., a healthcare setting where kiosk 409 and/or user device 402 is located), preferences of a particular clinician, any combination thereof, and/or the like. In some non-limiting embodiments or aspects, the smart algorithm may include at least one machine learning model, which may receive one or more of the aforementioned inputs and generate an output associate with the recommend medical devices 410 to be included in medical kit 414. For example, the machine learning model may learn about the ordering pattern of a particular clinician, facility, and/or the like and provide at least one recommendation, which may simplify the process of selecting medical devices 410 to be included in medical kit 414. In some non-limiting embodiments or aspects, kiosk 409 and/or user device 402 may categorize recommended medical kits 414 based on age group (e.g., adults, children, geriatric, and/or the like), co-morbidities (e.g., cardiovascular comorbidities (CVC)), medical procedure(s) (e.g., peripheral intravenous catheters (PIVC)), and/or patient medical condition(s) (e.g., hemophilia), and/or the like.

In some non-limiting embodiments or aspects, the user (e.g., medical personnel) may override the recommendation and/or elect to customize medical kit 414, as described herein. For example, for a hemophilia patient, the medical personnel may select additional wound dressings and/or the like. In some non-limiting embodiments or aspects, kiosk 409 and/or user device 402 may display a warning based on a patient's medical history. For example, for a hemophilia patient, the warning may indicate that the patient has a medical history of severe bleeding.

In some non-limiting embodiments or aspects, the user interface of kiosk 409 and/or user device 402 may be customizable. For example, the user interface may be selected from a list of templates. Additionally or alternatively, features (e.g., graphical elements) of the user interface may be customized to enable medical personnel to customize medical kits 414 based on requirements of the facility and/or medical personnel (e.g., based on a healthcare professional's and/or medical facility's requirement to ease clinical workflow, in accordance with facility protocols, and/or the like). For example, the user interface of a system placed in a general ward may be different from a system placed in a specialty ward based on the convenience of the specific facility. Additionally or alternatively, the user interface may be different based on the healthcare setting/ward (e.g., an intensive care unit (ICU) may have a different user interface than a gynecology ward).

In some non-limiting embodiments or aspects, in addition to or in lieu of user device 402 being integrated with kiosk 409, a portable and/or handheld device (e.g., a smartphone, a tablet, and/or the like) may be used as user device 402. For example, the portable and/or handheld device may receive (e.g., download, have installed thereof, and/or the like) and/or store a mobile application for medical personnel (e.g., a nurse, a doctor, hospital staff, pharmacy staff, and/or the like) to provide input to and/or output from kiosk 409. Additionally, the mobile application may include instructions (e.g., an instruction manual) and/or prompts to guide a user in using the mobile application.

In some non-limiting embodiments or aspects, kiosk 409 (e.g., storage grid 404 and/or receptacles 412 thereof) may be customized for a particular facility. For example, the size and/or number of receptacles 412 and/or the number of medical devices 410 stored by storage grid 404 may be customized based on the number of medical devices 410 (e.g., medical devices from different suppliers and/or manufacturers, medical consumables, etc.) anticipated to be used by the facility. In some non-limiting embodiments or aspects, receptacles 412 may be organized in slots and/or storage racks for medical devices 410 (e.g., from multiple different suppliers and/or manufacturers), the number and/or size of which may be customized as per requirements of the facility where kiosk 409 may be installed. In some non-limiting embodiments or aspects, the size of kiosk 409 (e.g., size of storage grid 404, number and/or size of receptacles 412, and/or the like) may be customized based on the size of the facility (e.g., number of patient beds, number of operating rooms, number of offices, and/or the like) where kiosk 409 is to be installed and/or based on consumption (e.g., historical consumption) of medical devices 410 at the facility.

In some non-limiting embodiments or aspects, kiosk 409 and/or sterilization and fulfillment device 408 may enable on-the-go sterilization of medical kits 414 (e.g., just before final dispensing). In some non-limiting embodiments or aspects, kiosk 409 and/or sterilization and fulfillment device 408 may have an option to sterilize or not sterilize. For example, bulk dispensing of non-sterile medical kits 414 may be performed, and medical kits 414 may later be sterilized on-the-go (e.g., as a last step before using). In some non-limiting embodiments or aspects, kiosk 409 may determine whether to sterilize medical kit 414 based on the type of medical kit 414 and/or the set of medical devices 410 therein.

In some non-limiting embodiments or aspects, the input received at kiosk 409 and/or user device 402 may include patient information (e.g., patient name, patient code, patient identifier, and/or the like) and/or procedure information (e.g., procedure code, procedure identifier, and/or the like).

In some non-limiting embodiments or aspects, the input received at kiosk 409 and/or user device 402 may include a time delay period. For example, the input may be received before medical kit 414 is desired to be dispensed (e.g., an hour before, a day before, and/or the like), and medical kit 414 may be dispensed after the time delay period (e.g., an hour, a day, and/or the like). In some non-limiting embodiments or aspects, medical kit 414 may be dispensed without delay (e.g., input received and/or medical kit 414 dispensed just before and/or during a medical procedure).

In some non-limiting embodiments or aspects, packaging the set of medical devices 410 may include packaging (e.g., by kiosk 409 and/or packaging device 406) the set of medical devices 410 in at least one container and/or sealing the container(s), as described herein. For example, the container may include at least one of a bag, a box, or any combination thereof. In some non-limiting embodiments or aspects, the container may include a bag of any suitable material, such as fabric, plastic, medical grade paper, any combination thereof, and/or the like. In some non-limiting embodiments or aspects, packaging device 406 may store packaging materials (e.g., containers, a roll of materials for making bags, and/or the like), and/or packaging device 406 may include robotic components (e.g., robotic arms, robotic hands, robotic claws, and/or the like) can retrieve the packaging materials, insert medical devices 410 into the packaging materials, and/or seal medical devices 410 in the packaging materials to form medical kit 414.

In some non-limiting embodiments or aspects, kiosk 409 (e.g., storage grid 404, packaging device 406, and/or sterilization and fulfillment device 408 thereof) may include additional safety features to identify if any medical devices 410 are damaged. Additionally or alternatively, kiosk 409 (e.g., storage grid 404, packaging device 406, and/or sterilization and fulfillment device 408 thereof) may determine whether the correct medical device(s) 410 are included in medical kit 414 (e.g., before dispensing medical kit 414). In some non-limiting embodiments or aspects, kiosk 409 (e.g., storage grid 404, packaging device 406, and/or sterilization and fulfillment device 408 thereof) may include at least one vision system (e.g., at least one camera, image capture device, laser system, and/or the like), which may scan each medical device 410, each medical kit 414, and/or the like to perform a quality check (e.g., check for damage, holes in packaging, and/or the like) for the quality of each medical device 410 and/or medical kit 414. Additionally or alternatively, kiosk 409 (e.g., storage grid 404, packaging device 406, and/or sterilization and fulfillment device 408 thereof) may discard the medical device 410 and/or medical kit 414 if the quality check identifies an issue (e.g., damage, holes in packaging, and/or the like).

In some non-limiting embodiments or aspects, kiosk 409 (e.g., storage grid 404 thereof) may enable maintaining and/or updating inventory automatically, as described herein. For example, kiosk 409 (e.g., storage grid 404) may monitor (e.g., track) medical devices 410 based on software and/or laser tracking. In some non-limiting embodiments or aspects, kiosk 409 (e.g., storage grid 404, packaging device 406, and/or sterilization and fulfillment device 408 thereof) may include at least one vision system (e.g., at least one camera, image capture device, laser system, and/or the like), which may count medical devices 410 and/or medical kits 414 that are dispensed and automatically update the inventory based on the count. In some non-limiting embodiments or aspects, kiosk 409 (e.g., storage grid 404, packaging device 406, and/or sterilization and fulfillment device 408 thereof) may communicate at least one alert indicating time to refill the inventory (e.g., if a count of medical devices satisfies a threshold amount, if a predetermined time period (e.g., weekly, monthly, and/or the like) has passed, and/or the like). In some non-limiting embodiments or aspects, kiosk 409 (e.g., storage grid 404, packaging device 406, and/or sterilization and fulfillment device 408 thereof) may communicate at least one communication if a medical device 410 has expired or will soon expire (e.g., within a predetermined time period from the expiration date) and/or if medical kit 414 includes a medical device 410 that has expired or will soon expired.

In some non-limiting embodiments or aspects, the packaging (e.g., container and/or wrapping) of each medical kit 414 may be color coded. For example, different colors may be used based on procedure type, patient type, patient location (e.g., a specific room, ward, and/or the like) and/or the like. Such color coding may enable easy identification and/or sorting of medical kits 414 (e.g., during transport).

Figure 5:
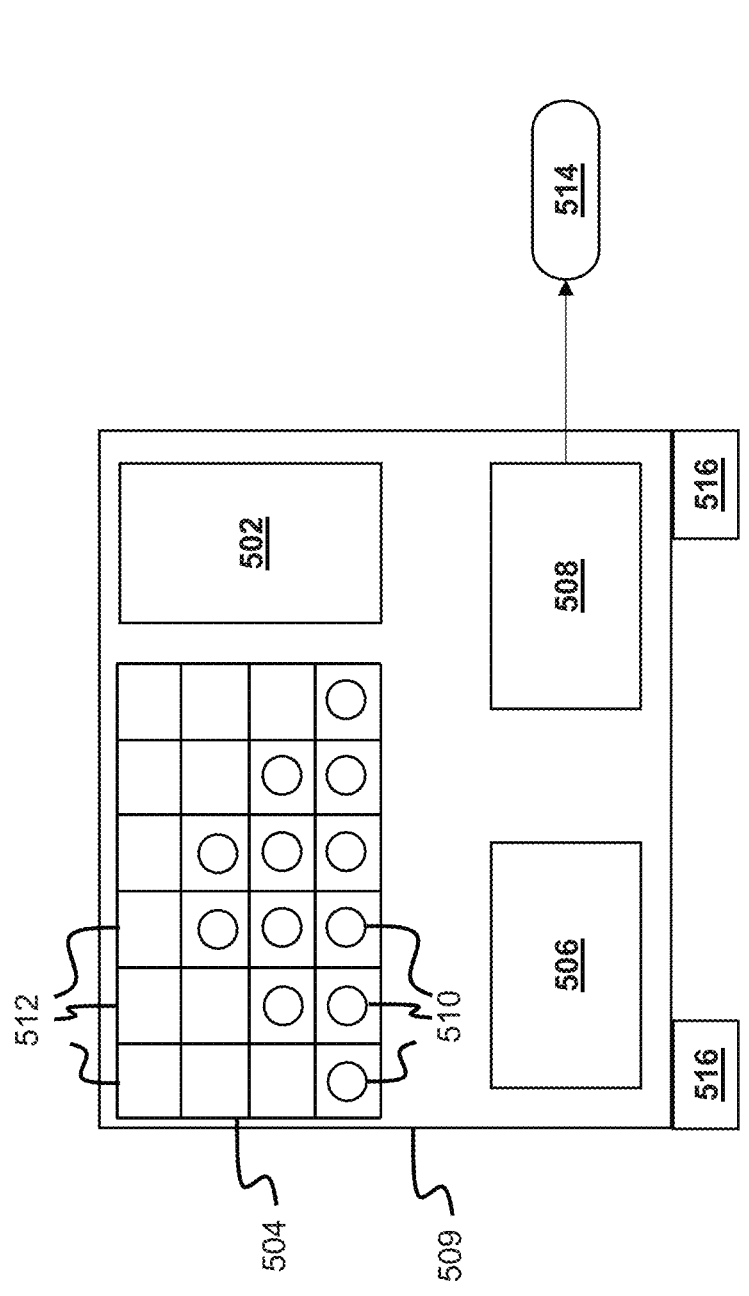
FIG. 5 is a diagram of an example implementation of the systems and/or methods for customized medical kit assembly and inventory management described herein, according to non-limiting embodiments or aspects of the presently disclosed subject matter.
Figure 5:
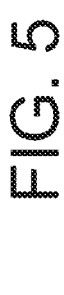

Referring now to FIG. 5, FIG. 5 is a diagram of an example implementation 500 of the systems and/or methods for customized medical kit assembly and inventory management described herein, according to some non-limiting embodiments or aspects of the presently disclosed subject matter. As shown in FIG. 5, implementation 500 may include user device 502, storage grid 504, packaging device 506, sterilization and fulfillment device 508, kiosk 509, medical devices 510, receptacles 512, medical kit 514, and/or at least one conveyance device 516. In some non-limiting embodiments or aspects, user device 502 may be the same as or similar to user device 102 and/or user device 402. In some non-limiting embodiments or aspects, storage grid 504 may be the same as or similar to storage grid 104 and/or storage grid 404. In some non-limiting embodiments or aspects, packaging device 506 may be the same as or similar to packaging device 106 and/or packaging device 406. In some non-limiting embodiments or aspects, sterilization and fulfillment device 508 may be the same as or similar to sterilization device 107, fulfillment device 108, and/or sterilization and fulfillment device 408. In some non-limiting embodiments or aspects, kiosk 509 may be the same as or similar to kiosk 109 and/or kiosk 409. In some non-limiting embodiments or aspects, medical devices 510 may be the same as or similar to medical devices 110 and/or medical devices 410. In some non-limiting embodiments or aspects, receptacles 512 may be the same as or similar to receptacles 112 and/or receptacles 412. In some non-limiting embodiments or aspects, medical kit 514 may be the same as or similar to medical kit 114 and/or medical kit 414. In some non-limiting embodiments or aspects, conveyance device 516 may be the same as or similar to conveyance device 416. The number and arrangement of components shown in FIG. 5 are provided as an example. In some non-limiting embodiments or aspects, implementation 500 may include additional components, fewer components, different components, or differently arranged components than those shown in FIG. 5. Additionally or alternatively, a set of components (e.g., one or more components) of implementation 500 may perform one or more functions described as being performed by another set of components of implementation 500.

As shown in FIG. 5, kiosk 509 may include at least one of user device 502, storage grid 504, packaging device 506, sterilization and fulfillment device 508, conveyance devices 516, and/or any combination thereof. For example, user device 502, storage grid 504, packaging device 506, sterilization and fulfillment device 508, and conveyance devices 516 each may be part of kiosk 509.

In some non-limiting embodiments or aspects, kiosk 509 may include a portable kiosk. For example, kiosk 509 may be configured to move and/or be moved to different locations within a facility (e.g., with conveyance devices 516), as described herein. In some non-limiting embodiments or aspects, the portable kiosk may include a robotic kiosk, as described herein. In some non-limiting embodiments or aspects, conveyance devices 516 may include wheels, motors (e.g., electric motors), robotic legs, or any other suitable conveyance devices to move kiosk 509 (and/or allow kiosk 509 to be moved).

In some non-limiting embodiments or aspects, kiosk 509 (e.g., user device 502 thereof) may be configured to receive an input associated with a selection of a set of medical devices 510 for medical kit 514, as described herein. Additionally or alternatively, kiosk 509 (e.g., storage grid 504 thereof) may be configured to dispense the set of medical devices 510 in response to receiving the input (e.g., in response to user device 502 receiving the input), as described herein. Additionally or alternatively, kiosk 509 (e.g., packaging device 506 thereof) may be configured to package the set of medical devices 510 (e.g., dispensed from storage grid 504) to form medical kit 514 and/or label medical kit 514, as described herein. Additionally or alternatively, kiosk 509 (e.g., sterilization and fulfillment device 508 thereof) may be configured to sterilize medical kit 514 and/or dispense medical kit 514, as described herein.

In some non-limiting embodiments or aspects, in addition to or in lieu of user device 502 being integrated with kiosk 509, a portable and/or handheld device (e.g., a smartphone, a tablet, and/or the like) may be used as user device 502, as described herein.

Figure 6:
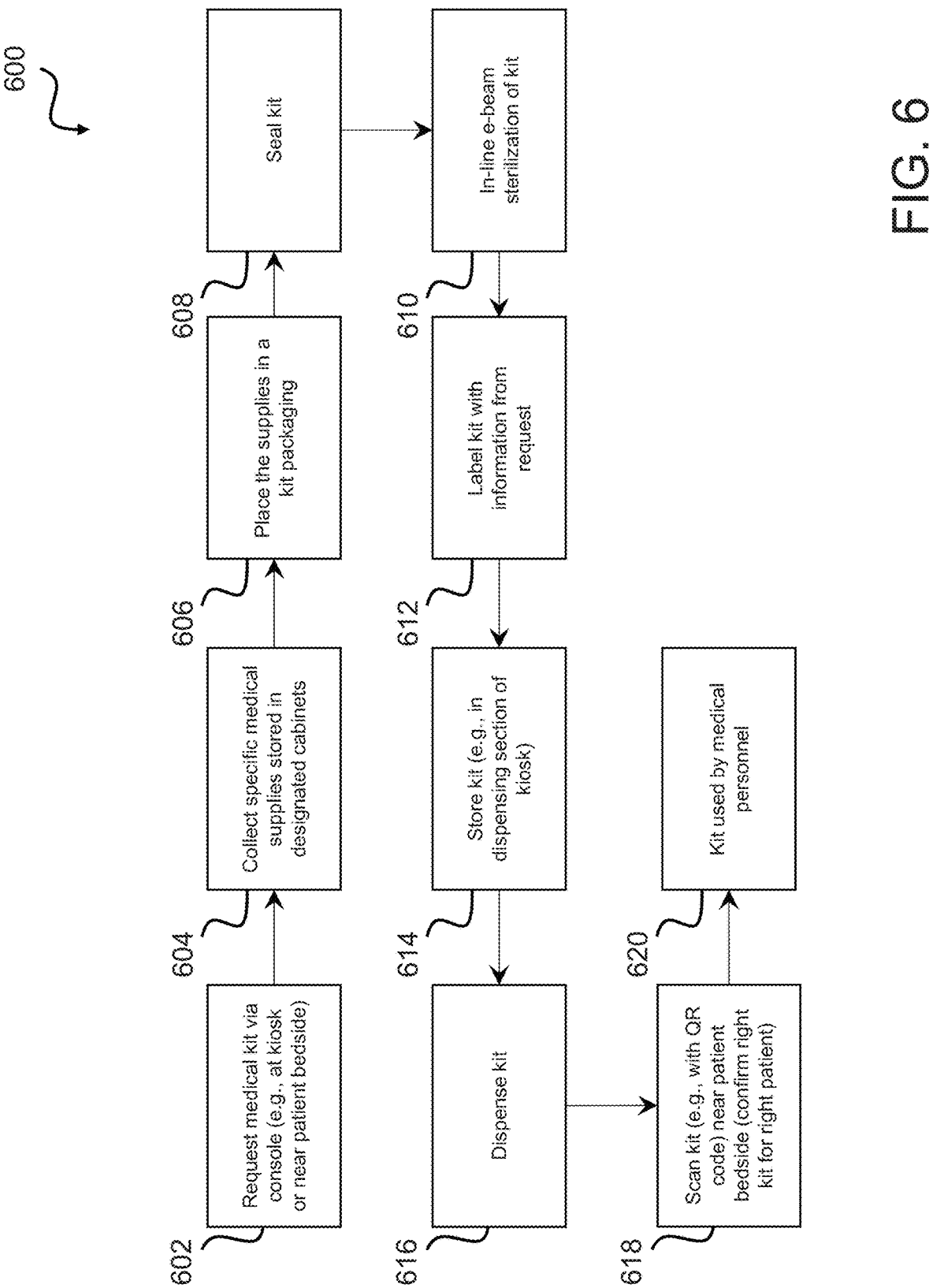
FIG. 6 is a flowchart of an example implementation of the systems and/or methods for customized medical kit assembly and inventory management described herein, according to non-limiting embodiments or aspects of the presently disclosed subject matter.

Referring now to FIG. 6, FIG. 6 is a flowchart of an example implementation 600 of the systems and/or methods for customized medical kit assembly and inventory management described herein, according to non-limiting embodiments or aspects of the presently disclosed subject matter. In some non-limiting embodiments or aspects, one or more of the steps of implementation 600 may be performed (e.g., completely, partially, and/or the like) by kiosk 109 (e.g., one or more devices of kiosk 109, such as user device 102, storage grid 104, packaging device 106, sterilization device 107, fulfillment device 108, and/or the like). In some non-limiting embodiments or aspects, one or more of the steps of implementation 600 may be performed (e.g., completely, partially, and/or the like) by another system, another device, another group of systems, or another group of devices, separate from or including kiosk 109, such as user device 102, storage grid 104, packaging device 106, sterilization device 107, fulfillment device 108, scanner 120, health information system 130 (e.g., one or more devices of health information system 130), database 132, and/or patient identification device 140. The number and arrangement of steps shown in FIG. 6 are provided as an example. In some non-limiting embodiments or aspects, implementation 600 may include additional steps, fewer steps, different steps, or differently arranged steps than those shown in FIG. 6.

As shown in FIG. 6, at step 602, implementation 600 may include requesting a medical kit via a console (e.g., user device 102 and/or the like). For example, medical personnel may provide input to the console (e.g., user device 102) to select a recommended set of medical devices 110 and/or a customized set of medical devices 110, as described herein.

In some non-limiting embodiments or aspects, the console (e.g., user device 102) may be at a patient location (e.g., patient bedside). Additionally or alternatively, the console may be at and/or part of kiosk 109 and/or storage grid 104.

As shown in FIG. 6, at step 604, implementation 600 may include collecting specific medical supplies (e.g., medical devices 110) stored in designated cabinets (e.g., receptacles 112). For example, storage grid 104 and/or kiosk 109 may dispense the medical supplies (e.g., medical devices 110) from cabinets (e.g., receptacles 112) of storage grid 104, as described herein.

As shown in FIG. 6, at step 606, implementation 600 may include placing the medical supplies (e.g., medical devices 110) in kit packaging (e.g., to form medical kit 114). For example, packaging device 106 and/or kiosk 109 may package the medical supplies (e.g., medical devices 110) in kit packaging, as described herein.

As shown in FIG. 6, at step 608, implementation 600 may include sealing the kit (e.g., medical kit 114). For example, packaging device 106 and/or kiosk 109 may seal the packaging (e.g., seal medical kit 114), as described herein.

As shown in FIG. 6, at step 610, implementation 600 may include in-line e-beam sterilization of the kit (e.g., medical kit 114). For example, sterilization device 107 and/or kiosk 109 may sterilize medical kit 114 with e-beam sterilization, as described herein.

As shown in FIG. 6, at step 612, implementation 600 may include labelling the kit (e.g., medical kit 114) with information from the request (e.g., the input received by user device 102). For example, packaging device 106, fulfillment device 108, and/or kiosk 109 may label medical kit 114, as described herein.

As shown in FIG. 6, at step 614, implementation 600 may include storing the kit (e.g., medical kit 114). For example, fulfillment device 108, storage grid 104, and/or kiosk 109 may store medical kit 114, as described herein.

As shown in FIG. 6, at step 616, implementation 600 may include dispensing the kit. For example, fulfillment device 108 and/or kiosk 109 may dispense medical kit 114, as described herein.

As shown in FIG. 6, at step 618, implementation 600 may include scanning the kit (e.g., medical kit 114) near a patient location (e.g., patient bedside). For example, scanner 120 may scan the label and/or tag (e.g., QR code and/or the like) of medical kit 114 and/or communicate data based on scanning the label and/or tag to health information system 130 and/or kiosk 109, as described herein. In some non-limiting embodiments, scanner 120, health information system 130, and/or kiosk 109 may determine whether (e.g., confirm that) medical kit 114 is the correct (e.g., right) kit for the patient (e.g., based on scanning the label and/or tag), as described herein.

As shown in FIG. 6, at step 620, implementation 600 may include using the kit (e.g., medical kit 114). For example, medical personnel may use medical kit 114 and/or the set of medical devices 110 therein (e.g., for at least one medical procedure), as described herein.

Referring now to FIG. 7, FIG. 7 is a flowchart of an example implementation 700 of the systems and/or methods for customized medical kit assembly and inventory management described herein, according to non-limiting embodiments or aspects of the presently disclosed subject matter. In some non-limiting embodiments or aspects, one or more of the steps of implementation 700 may be performed (e.g., completely, partially, and/or the like) by kiosk 109 (e.g., one or more devices of kiosk 109, such as user device 102, storage grid 104, packaging device 106, sterilization device 107, fulfillment device 108, and/or the like). In some non-limiting embodiments or aspects, one or more of the steps of implementation 700 may be performed (e.g., completely, partially, and/or the like) by another system, another device, another group of systems, or another group of devices, separate from or including kiosk 109, such as user device 102, storage grid 104, packaging device 106, sterilization device 107, fulfillment device 108, scanner 120, health information system 130 (e.g., one or more devices of health information system 130), database 132, and/or patient identification device 140. The number and arrangement of steps shown in FIG. 7 are provided as an example. In some non-limiting embodiments or aspects, implementation 700 may include additional steps, fewer steps, different steps, or differently arranged steps than those shown in FIG. 7.

As shown in FIG. 7, at step 702, implementation 700 may include medical personnel preparing (e.g., initiating) a request for a kit (e.g., medical kit 114). For example, medical personnel may provide input to the console (e.g., user device 102) to start the process of requesting medical kit 114.

In some non-limiting embodiments or aspects, the console (e.g., user device 102) may be at a patient location (e.g., patient bedside). Additionally or alternatively, the console may be at and/or part of kiosk 109 and/or storage grid 104.

As shown in FIG. 7, at step 704, implementation 700 may include recommending a kit (e.g., a recommended set of medical devices 110 for medical kit 114). For example, kiosk 109, user device 102, and/or health information system 130 may generate a recommended set of medical devices 110, as described herein. For example, kiosk 109, user device 102, and/or health information system 130 may generate the recommended set of medical devices 110 based on input received from a user (e.g., medical personnel, such as a nurse, a clinician, and/or the like) and/or data stored in database 132, as described herein. For example, the input received from the user and/or data stored in database 132 may include at least one of a selected medical procedure, demographic data associated with a patient, medical history data associated with the patient, preference data associated with a clinician, preference data associated with a facility, medical kit history data associated with the clinician, medical kit history data associated with the facility, any combination thereof, and/or the like. In some non-limiting embodiments or aspects, kiosk 109, user device 102, and/or health information system 130 may display a graphical user interface comprising the recommended set of medical devices, as described herein.

As shown in FIG. 7, at step 706, implementation 700 may include medical personnel selecting the recommended kit (e.g., the recommended set of medical devices 110 for medical kit 114) and/or opting for a custom kit (e.g., medical kit 114). For example, kiosk 109, user device 102, and/or health information system 130 may receive a first input (e.g., via the graphical user interface) associated with selecting the recommended set of medical devices 110 as the selected set of medical devices 110 for medical kit 114 (e.g., the user selects the medical devices 110 as recommended by kiosk 109, user device 102, and/or health information system 130), as described herein. Alternatively, kiosk 109, user device 102, and/or health information system 130 may receive a second input (e.g., via the graphical user interface) indicating that the user is not selecting the recommended set of medical devices 110 and/or indicating that the user would like to select a custom set of medical devices 110 for medical kit 114, as described herein.

As shown in FIG. 7, at step 708, implementation 700 may include medical personnel submitting a request for a medical kit. For example, medical personnel may provide input to the console (e.g., user device 102) to select a recommended set of medical devices 110 and/or a customized set of medical devices 110, as described herein. Additionally or alternatively, after making the selection, medical personnel may provide input to the console (e.g., user device 102) to submit the request for medical kit 114.

As shown in FIG. 7, at step 710, implementation 700 may include receiving the request and/or preparing the kit. For example, kiosk 109, user device 102, and/or storage grid 104 may receive the submitted request. Additionally or alternatively, kiosk 109 and/or storage grid 104 may dispense the set of medical devices 110 in response to receiving the request. Additionally or alternatively, kiosk 109 and/or packaging device 106 may package the set of medical devices 110 (e.g., dispensed from storage grid 104) to form medical kit 114 and/or label medical kit 114, as described herein. Additionally or alternatively, kiosk 109, sterilization device 107 may sterilize medical kit 114, as described herein.

As shown in FIG. 7, at step 712, implementation 700 may include dispensing the kit. For example, kiosk 109 and/or fulfillment device 108 may dispense medical kit 114.

In some non-limiting embodiments or aspects, medical kit 114 and/or medical devices 110 therein may be credited to the patient, health information system 130 may be updated, and/or the inventory (e.g., stored by health information system 130, kiosk 109, and/or storage grid 104) may be updated, as described herein.

Although the disclosed subject matter has been described in detail for the purpose of illustration based on what is currently considered to be the most practical and preferred embodiments or aspects, it is to be understood that such detail is solely for that purpose and that the disclosed subject matter is not limited to the disclosed embodiments or aspects but, on the contrary, is intended to cover modifications and equivalent arrangements that are within the spirit and scope of the appended claims. For example, it is to be understood that the presently disclosed subject matter contemplates that, to the extent possible, one or more features of any embodiment or aspect can be combined with one or more features of any other embodiment.

What is claimed is:

1. A system for customized medical kit assembly and inventory management, comprising:
   a user device configured to receive an input associated with a selection of a set of medical devices for a medical kit;
   a storage grid configured to dispense the set of medical devices in response to receiving the input;
   a packaging device configured to package the set of medical devices dispensed from the storage grid to form the medical kit; and
   a fulfillment device configured to dispense the medical kit.

2. The system of claim 1, wherein the user device comprises an input component of a kiosk, and wherein the kiosk comprises the storage grid, the packaging device, and the fulfillment device.

3. The system of claim 2, wherein the kiosk comprises a stationary kiosk.

4. The system of claim 2, wherein the kiosk comprises a portable kiosk.

5. The system of claim 4, wherein the portable kiosk comprises a robotic kiosk.

6. The system of claim 1, wherein the user device comprises an input component of a kiosk, and wherein the input component comprises at least one of a touch screen display, a keyboard, a keypad, a mouse, a button, a switch, a microphone, a camera, or any combination thereof.

7. The system of claim 1, wherein the user device comprises at least one of a computing device, a portable computing device, a handheld computing device, a personal digital assistant (PDA), a smartphone, a tablet, or any combination thereof.

8. The system of claim 1, wherein the storage grid comprises a plurality of receptacles, each receptacle containing at least one medical device of a plurality of medical devices, wherein the set of medical devices comprises a subset of the plurality of medical devices.

9. The system of claim 1, wherein packaging the set of medical devices comprises:

packaging the set of medical devices in at least one container; and sealing the at least one container.

10. The system of claim 9, wherein the at least one container comprises at least one of a bag, a box, or any combination thereof.

11. The system of claim 1, wherein packaging the set of medical devices comprises wrapping the set of medical devices.

12. The system of claim 1, wherein packaging the set of medical devices dispensed from the storage grid to form the medical kit comprises labeling the medical kit.

13. The system of claim 12, wherein labeling the medical kit comprises affixing at least one of a machine-readable optical label, a radio frequency identification (RFID) tag, or any combination thereof to the medical kit.

14. The system of claim 13, wherein the machine-readable optical label comprises at least one of a barcode, a quick response (QR) code, or any combination thereof.

15. The system of claim 13, wherein the RFID tag comprises at least one of an RFID tag with an integrated circuit (IC) storing identification data, a chipless RFID tag, or any combination thereof.

16. The system of claim 12, further comprising a scanner configured to scan the labeled medical kit at a patient location.

17. The system of claim 1, further comprising at least one conveyance device configured to at least one of:

convey the set of medical devices dispensed from the storage grid to the packaging device; or convey the medical kit to the fulfillment device.

18. The system of claim 17, wherein the at least one conveyance device comprises at least one of a conveyor belt, a robotic arm, or any combination thereof configured to convey the set of medical devices dispensed from the storage grid to the packaging device.

19. The system of claim 17, wherein the at least one conveyance device comprises at least one of a conveyor belt, a robotic arm, or any combination thereof configured to convey the medical kit to the fulfillment device.

20. The system of claim 1, wherein the fulfillment device comprises a robotic fulfillment device configured to convey the medical kit to a fulfillment location.

21. The system of claim 1, further comprising at least one sterilization device configured to sterilize the medical kit before the medical kit is dispensed by the fulfillment device.

22. The system of claim 21, wherein the at least one sterilization device comprises at least one of an electron beam (e-beam) sterilization device, an ethylene oxide (ETO) sterilization device, a gamma irradiation sterilization device, or any combination thereof.

23. The system of claim 1, wherein the user device is further configured to:

generate a recommended set of medical devices based on at least one of a selected medical procedure, demographic data associated with a patient, medical history data associated with the patient, preference data associated with a clinician, preference data associated with a facility, medical kit history data associated with the clinician, medical kit history data associated with the facility, or any combination thereof; and display a graphical user interface comprising the recommended set of medical devices, wherein receiving the input associated with the selection of the set of medical devices for the medical kit comprises receiving a first input associated with selecting the recommended set of medical devices as the set of medical devices for the medical kit.

24. The system of claim 1, wherein the user device is further configured to:

display a graphical user interface comprising a listing of a plurality of medical devices; and receive a first input associated with selecting a subset of the plurality of medical devices, wherein the set of medical devices comprises the subset of the plurality of medical devices.

25. The system of claim 1, further comprising a health information system configured to credit the set of medical devices to a patient based on dispensing the medical kit.

26. The system of claim 1, wherein the storage grid is further configured to store a plurality of medical devices and the set of medical devices comprises a subset of the plurality of medical devices, the system further comprises a health information system configured to update an inventory of medical devices stored by the storage grid based on dispensing the medical kit.

27. A computer program product for customized medical kit assembly and inventory management, comprising at least one non-transitory computer-readable medium including one or more instructions that, when executed by at least one processor, cause the at least one processor to:

receive, from a user device, an input associated with a selection of a set of medical devices for a medical kit;

dispense, from a storage location, the set of medical devices in response to receiving the input;

package, at a packaging location, the set of medical devices dispensed from the storage location to form the medical kit; and dispense, from a fulfillment location, the medical kit.

* * * * *